United States Patent [19]

Hiyama et al.

[11] Patent Number: 5,369,109

[45] Date of Patent: Nov. 29, 1994

[54] OPTICALLY ACTIVE ESTERS OF 7-SUBSTITUTED 3,5-DIFUNCTIONALIZED 6-HEPTENOIC ACIDS

[75] Inventors: Tamejiro Hiyama; Tatsuya Minami, both of Sagamihara; Takeshi Hanamoto, Okazaki, all of Japan; Guntoori B. Reddy, Montreal, Canada

[73] Assignee: Sagami Chemical Research Center, Tokyo, Japan

[21] Appl. No.: 77,454

[22] Filed: Jun. 17, 1993

Related U.S. Application Data

[62] Division of Ser. No. 748,076, Aug. 21, 1991, Pat. No. 5,276,154.

[30] Foreign Application Priority Data

Aug. 30, 1990 [JP] Japan ................................. 2-226741
Aug. 1, 1991 [JP] Japan ................................. 3-214148

[51] Int. Cl.$^5$ ...................... A01N 43/40; C07C 69/73; C07D 215/06; C07D 471/04
[52] U.S. Cl. .................................... 514/277; 514/301; 514/303; 514/311; 514/312; 514/345; 514/511; 546/114; 546/119; 546/153; 546/174; 546/285; 546/301; 560/60; 560/183
[58] Field of Search ............... 514/311, 338, 277, 301, 514/303, 312, 345, 511; 546/174, 270, 271, 114, 119, 153, 174, 285, 301; 560/60, 183

[56] References Cited

U.S. PATENT DOCUMENTS 4,855,481 8/1989 Guidon et al. .................... 560/55

FOREIGN PATENT DOCUMENTS 0324347 4/1989 European Pat. Off. .

OTHER PUBLICATIONS

Taber, Chemical Abstracts, 23309r, vol. 109, No. 3, Jul. 18, 1988.
Hiyama et al., Abstract of the meeting of Jan. 22, 1991 of the 116th Committee, Japan Assc. for the Promotion of Science.

Primary Examiner—Marianne M. Cintins
Assistant Examiner—Phyllis G. Spivack
Attorney, Agent, or Firm—Nixon & Vanderhye

[57] ABSTRACT

The present invention provides optically active esters of 7-substituted 3,5-difunctionalized 6-heptenoic acids represented by the following formula:

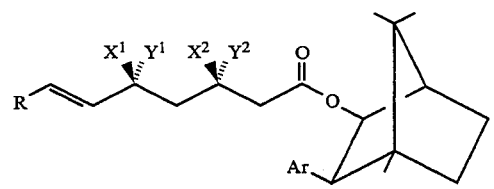

wherein
R is a substituted or unsubstituted aromatic group, a substituted or unsubstituted heteroaromatic group or a substituted vinyl group;
Ar is a condensed aromatic group;
$X^1$ and $Y^1$ are not the same and each is a hydrogen atom or a hydroxyl group; and
$X^2$ and $Y^2$ are not the same and each is a hydrogen atom or a hydroxyl group or enantiomers thereof.

5 Claims, No Drawings

OPTICALLY ACTIVE ESTERS OF 7-SUBSTITUTED 3,5-DIFUNCTIONALIZED 6-HEPTENOIC ACIDS

This is a division of application Ser. No. 07/748,076, filed Aug. 21, 1991 now U.S. Pat. No. 5,276,154.

BACKGROUND OF THE INVENTION

The present invention relates to optically active esters of 7-substituted 3,5-difunctionalized 6-heptenoic acids including esters of β,δ-diketocarboxylic acids and reduced products thereof. The esters are useful as intermediates for preparing therapeutical agents which inhibit HMG-CoA reductase and are potent for hypercholesterolemia.

For example, optically active esters of β,δ-syn-dihydroxycarboxylic acids according to the present invention represented by the following formula (IV):

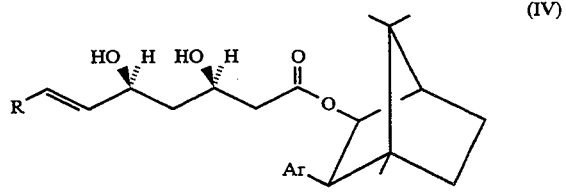

wherein
R is a substituted or unsubstituted aromatic group, a substituted or unsubstituted heteroaromatic group or a substituted vinyl group; and
Ar is a condensed aromatic group, or optically active enantio-esters of β,δ-syn-dihydroxycarboxylic acids represented by the following formula (V'):

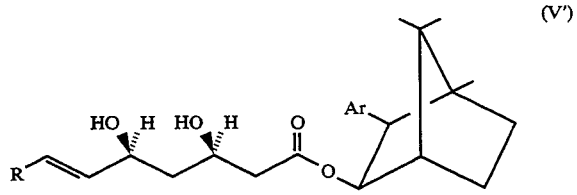

wherein R and Ar are the same as above, can be converted into 7-substituted (3R, 5S, 6E)-3,5-dihydroxy-6-hepten-5-olides having an inhibitory activity of HMG-CoA reductase or their enantiomers by hydrolyzing the compounds (IV) or (V'), or their enantiomers, followed by lactonizing the resulting acids.

Furthermore, optically active esters of β,δ-syn-dihydroxycarboxylic acids of the formula (IV) or (V'), or their enantiomers can also be utilized for preparing an insect pheromone, endo-1,3-dimethyl-2,9-dioxabicyclo[3.3.1]nonane as described in Tetrahedron Lett., 28, 4773 (1987); ibid., 21, 3013 (1980); J. Org. Chem., 54, 2238 (1989); Chem. Pharm. Bull., 37, 1078 (1989); and Helv. Chim. Acta., 72, 1284 (1989).

Optically active 7-substituted (3R, 5S, 6E)-3,5-dihydroxy-6-hepten-1,5-olides having an inhibitory activity of HMG-CoA reductase have been prepared via either of the following processes:

(1) protecting (2S, 4R)-4-hydroxy-6-methoxy-tetrahydropyran-2-carbaldehyde, followed by subjecting the protected compound to the Wittig reaction, hydrolysis and oxidation, successively [J. Med. Chem., 33, 52 (1990)]; or (2) obtaining a lower alkyl ester or aryl ester of 7-substituted (3R, 5S, 6E)-3,5-dihydroxy-6-heptenoic acid, followed by hydrolyzing the ester [for example, EP 319,847; EP 324,347; J. Med. Chem., 32, 2038 (1989)].

In the above process (1), the source of the optical activity is sugar derivatives [Tetrahedron Lett., 31, 1869 (1990); ibid., 30, 6015 (1989); ibid., 26, 4995, 2947 (1985)], glutamic acid [J. Chem. Soc., Chem. Commun., 1988, 1417], or ascorbic acid [Tetrahedron Lett., 26, 2951 (1985)], of which functional groups are suitably transformed so that desired precursors are attained. Although the sources are easily available natural products and thus inexpensive, multi-step operations are required for removing unnecessary functional groups and transforming the carbon skeletons in order to obtain the desired precursors. Therefore, the process is less attractive.

The precursor of the above process (2) is often prepared as a racemic mixture. Therefore, the process requires optical resolution for obtaining the desired [3R, 5S] enantiomer with the expense of the other [3S, 5R] enantiomer [J. Med. Chem., 29, 159 (1986)]. Asymmetric synthesis of the [3R, 5S] enantiomer is achieved by repeating asymmetric aldol condensation of a chiral acetic acid ester with an aldehyde twice [Tetrahedron Lett., 28, 1385 (1987)], by converting a chiral β-hydroxyester into a chiral δ-hydroxy-β-ketoester, followed by stereoselective syn-reduction [Tetrahedron Lett., 31, 2545 (1990); ibid., 30, 5115 (1989); Japanese Patent Application Laying Open (KOKAI) Nos. 199945/89, 213270/89; U.S. Pat. No. 4,855,481], or by asymmetric epoxydation of an allylic alcohol [Tetrahedron Lett., 28, 703, 291 (1987)]. These methods, however, require inevitable multi-step operations for transforming the carbon skeletons and controlling the stereochemistry.

The optically active esters of β,δ-syn-dihydroxycarboxylic acid are important as precursors for preparing 7-substituted (3R, 5S, 6E)-3,5-dihydroxy-6-hepten-1,5-olides and endo-1,3-dimethyl-2,9-dioxabicyclo[3.3.1]nonane as described above. A short-step synthesis of racemic lower alkyl esters of β,δ-syn-dihydroxycarboxylic acid has been reported which comprises a stereoselective syn-reduction of the corresponding lower alkyl esters of β,δ-diketocarboxylic acid [Japanese Patent Application Laying Open (KOKAI) No. 165547/89]. However, the method is not applicable to asymmetric synthesis of the esters of β,δ-syn-dihydroxycarboxylic acid [Tetrahedron Lett., 29, 6467 (1988)]. This is due to the planar structure of the molecules of the β,δ-diketocarboxylic acid esters and to the absence of the known reducing agent or catalyst which may distinguish the Re face and the Si face of the two carbonyl groups. Accordingly, lower alkyl esters of 7-substituted β,δ-diketo-6-heptenoic acid are not attractive as precursors of desired 7-substituted (3R, 5S, 6E)-3,5-dihydroxy-6-hepten-5olides and their enantiomers.

Thus, these known methods for preparing optically active heptenolides require tedious multi-step operations and/or optical resolutions of racemic compounds with losing undesired enantiomers.

As a result of the extensive studies, the present inventors have found that an ester of a β,δ-diketocarboxylic acid or a β-hydroxy-δ-ketocarboxylic acid with a 2-exo-aryl-3-exo-hydroxybornane is useful as a precursor of the optically active ester of β,δ-syn-dihydroxycarboxylic acid of the formula (IV) or (V') and that the latter compound is easily converted into the finally desired lactone. The both enantiomers of 2-exo-aryl-3-exo-hydroxybornane are easily obtainable from (+)- or (−)-camphor.

SUMMARY OF THE INVENTION

Specifically, the present invention provides an optically active ester with 2-exo-aryl-3-exo-hydroxybornane represented by the following formula (I):

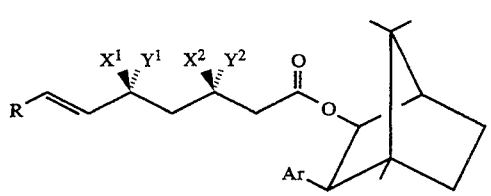
(I)

wherein
R is a substituted or unsubstituted aromatic group, a substituted or unsubstituted heteroaromatic group or a substituted vinyl group;
Ar is a condensed aromatic group;
$X^1$ and $y^1$ are not the same and each is a hydrogen atom or a hydroxyl group, or may be combined to represent an oxygen atom which forms a carbonyl group together with the carbon atom to which $X^1$ and $y^1$ are attached; and $X^2$ and $y^2$ are not the same and each is a hydrogen atom or a hydroxyl group, or may be combined to represent an oxygen atom which forms a carbonyl group together with the carbon atom to which $X^2$ and $y^2$ are attached, or an enantiomer thereof.

The specific types of the above ester include: (i) an optically active ester of $\beta,\delta$-diketocarboxylic acid represented by the following formula (II):

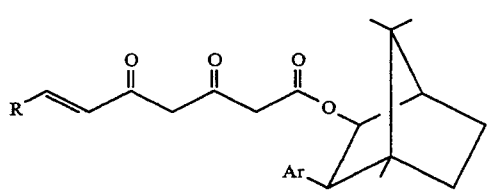
(II)

wherein
R is a substituted or unsubstituted aromatic group, a substituted or unsubstituted heteroaromatic group or a substituted vinyl group; and
Ar is a condensed aromatic group, or an enantiomer thereof;

(ii) an optically active ester of $\beta$-hydroxy-$\delta$-ketocarboxylic acid represented by the following formula (III):

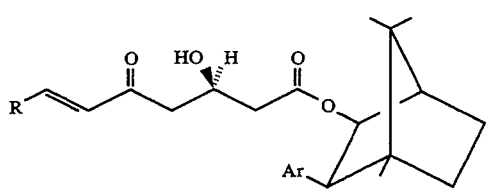
(III)

wherein

R is a substituted or unsubstituted aromatic group, a substituted or unsubstituted heteroaromatic group or a substituted vinyl group; and
Ar is a condensed aromatic group, or an enantiomer thereof;

(iii) an optically active ester of $\beta,\delta$-syn-dihydroxycarboxylic acid represented by the following formula (IV):

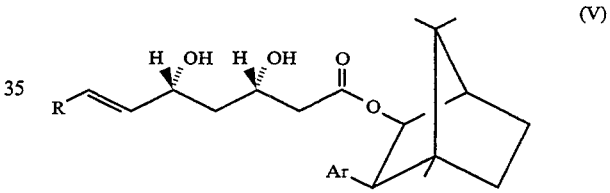
(IV)

wherein
R is a substituted or unsubstituted aromatic group, a substituted or unsubstituted heteroaromatic group or a substituted vinyl group; and
Ar is a condensed aromatic group, or an enantiomer thereof;

(iv) an optically active enantio-ester of $\beta,\delta$-syn-dihydroxycarboxylic acid represented by the following formula (V):

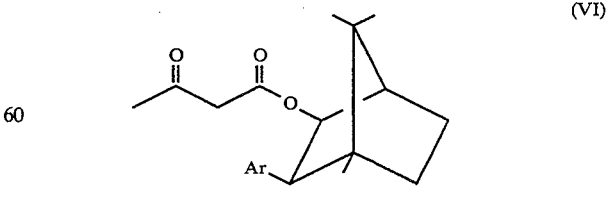
(V)

wherein
R is a substituted or unsubstituted aromatic group, a substituted or unsubstituted heteroaromatic group or a substituted vinyl group;
Ar is a condensed aromatic group, or an enantiomer thereof.

The invention also provides a process for preparing an optically active ester of $\beta,\delta$-diketocarboxylic acid of the formula (II) or its enantiomers, which comprises treating an optically active ester of acetoacetic acid or its enantiomer represented by the following formula (VI):

(VI)

wherein Ar is the same as above, with one or more bases, followed by condensing resulting dianion with an N-methoxyamide represented by the following formula (VII):

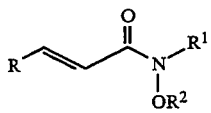

(VII)

wherein

R is the same as above;

each of $R^1$ and $R^2$ is a straight or branched alkyl group of 1 to 4 carbon atoms.

The invention further provides a process for preparing an optically active ester of β-hydroxy-δ-ketocarboxylic acid of the formula (III) or its enantiomer, which comprises stereoselectively reducing an optically active ester of β,δ-diketocarboxylic acid of the formula (II) or its enantiomers using an aluminium hydride compound represented by the formula: $HAlR^3{}_2$ as reducing agent, where $R^3$ is a straight or branched alkyl group of 1 to 8 carbon atoms.

The present invention also provides a process for preparing an optically active ester of β,δ-syn-dihydroxycarboxylic acid of the formula (IV) or its enantiomer, which comprise stereoselectively reducing an optically active ester of β-hydroxy-δ-ketocarboxylic acid of the formula (III) or its enantiomer using sodium borohydride as reducing agent in the presence of an organoboron compound represented by the formula: $R^4{}_2BZ^1$ where $R^4$ is a straight or branched alkyl group of 1 to 8 carbon atoms and $Z^1$ is a halogen atom or an alkoxy group having 1 to 8 carbon atoms.

The present invention still provides a process for preparing an optically active ester of β,δ-syn-dihydroxycarboxylic acid of the formula (IV) or its enantiomer, which comprise stereoselectively reducing an optically active ester of β,δ-diketocarboxylic acid of the formula (II) or its enantiomer using sodium borohydride as reducing agent in the presence of an organoboron compound represented by the formula: $R^5{}_2BZ^2$ where $R^5$ is a straight or branched alkyl group of 2 to 8 carbon atoms and $Z^2$ is a halogen atom or an alkoxy group having 1 to 8 carbon atoms.

The present invention still further provides a process for preparing an optically active enantio-ester of β,δ-syn-dihydroxycarboxylic acid of the formula (V) or its enantiomer, which comprises stereoselectively reducing an optically active ester of β,δ-diketocarboxylic acid of the formula (II) or its enantiomer using sodium borohydride as reducing agent in the presence of an organoboron compound represented by the formula: $Me_2BZ^3$ where $Z^3$ is a halogen atom or an alkoxy group having 1 to 8 carbon atoms.

The optically active esters according to the invention are useful as precursors for preparing 7-substituted (3R, 5S, 6E)-3,5-dihydroxy-6-hepten-1,5-olides having an inhibitory activity of HMG-CoA reductase and their enantiomers as well as a sex-attractant pheromone of beetles, endo-1,3-dimethyl-2,9-dioxabicyclo[3.3.1]nonane in high optical yields without requiring tedious and material-consuming optical resolution.

Accordingly, the present invention also provides a use of the optically active ester of β,δ-syn-dihydroxycarboxylic acid of the formula (IV) or (V), or enantiomer thereof as the precursor for preparing the 7-substituted (3R, 5S, 6E)-3,5-dihydroxy-6-hepten-5-olide or the enantiomer thereof which comprises hydrolyzing the optically active ester, followed by lactonization.

DETAILED DESCRIPTION OF THE INVENTION

The compounds according to the present invention are represented by the above formula (I), specifically formulae (II), (III), (IV) and (V), or as their enantiomers.

The aromatic group of R may have 6 to 18 carbon atoms in the aromatic ring and optionally be condensed with one or more other aromatic rings such as benzene or naphthalene. The heteroaromatic group of R may be five- or six-membered and optionally be condensed with one or more other aromatic rings or heteroaromatic rings such as benzene, naphthalene, pyridine, pyrimidine, pyrazine, pyrazole, or thiophene.

The examples of the substituents in the substituted aromatic or heteroaromatic group or the substituted vinyl group include alkyl groups having 1 to 6 carbon atoms; cycloalkyl groups having 3 to 8 carbon atoms; halogen atoms; alkoxy groups having 1 to 6 carbon atoms; phenyl groups optionally substituted with one or more alkyl groups having 1 to 6 carbon atoms, halogen atoms, alkoxy groups having 1 to 6 carbon atoms and combination thereof.

The number of the substitution in the substituted aromatic or heteroaromatic group may be one to five, preferably one to three. That in the substituted vinyl group is one to three.

The examples of R in the above formulae include phenyl group; substituted phenyl groups such as 4-tolyl, 4-chlorophenyl, 4-methoxyphenyl, 3,5-dichloro-6-(4-fluorophenyl)phenyl, 2,4-dimethyl-6-(4-fluoro-3-methylphenyl) phenyl; substituted indolyl groups such as 3-(4-fluorophenyl)-1-isopropylindol-2-yl; substituted pyridyl groups such as 4-phenyl-2-methylpyridin-3-yl, 2-isopropyl-6-phenyl-4-(4-fluorophenyl)pyridin-3-yl, 2,5-diisopropyl-4-(4-fluorophenyl)pyridin-3-yl, 2,6-diisopropyl-4-(4-fluorophenyl)-5-benzyloxymethylpyridin-3-yl, 6-cyclopropyl-4-(4-fluorophenyl)-1,3-dimethylpyrazolo[3,4-b]pyridin-5-yl, 4-(4-fluorophenyl)-1,3-dimethyl-6-(1-methylethyl)pyrazolo[3,4-b]pyridin-5-yl, 1-t-butyl-6-cyclopropyl-4-(4-fluorophenyl)-3-methylpyrazolo[3,4-b]pyridin-5-yl, 1-t-butyl-6-cyclopropyl-4-(4-fluorophenyl)-3-phenylpyrazolo[3,4-b]pyridin-5-yl, 6-cyclopropyl-4-(4-fluorophenyl)thieno[2,3-b]pyridin-5-yl, 6-cyclopropyl-3-ethyl-4-(4-fluorophenyl)-2-methylthieno[2,3-b]pyridin-5-yl; substituted pyrimidyl groups such as 6-isopropyl-2-phenyl-4-(4-fluorophenyl)pyrimidin-5-yl, 6-methyl-2-phenyl-4-(4-fluorophenyl)pyrimidin-5-yl, 2,4-dimethyl-6-(4-fluorophenyl)pyrimidin-5-yl; substituted quinolyl groups such as 3-isopropyl-1-(4-fluorophenyl)-4-oxoquinolin-2-yl, 2-cyclopropyl-4-(4-fluorophenyl)quinolin-3-yl, 4-(4-fluorophenyl)-2-(1-methylethyl)quinolin-3-yl,6-chloro-2-(1-methylethyl)-4-phenylquinolin-3-yl, 4-(4-fluorophenyl)-6-methyl-2-(1-methylethyl)quinolin-3-yl, 2-cyclopropyl-4-(4-fluorophenyl)-8-methylquinolin-3-yl; substituted pyrazolyl groups such as 5-(4-fluorophenyl)-3-isopropyl-1-phenylpyrazol-4-yl; substituted pyridazyl groups such as 3,4-bis(4-fluorophenyl)-6-isopropylpyridazin-5-yl; substituted imidazolyl groups such as 4-isopropyl-2-phenyl-1-(4-fluorophenyl)-1H-imidazol-5-yl; substituted pyrrolyl groups such as 2-isopropyl-1-phenyl-4-(4-fluorophenyl)pyrrol-3-yl, 1-isopropyl-3,4-bis(4-fluorophenyl)pyrrol-2,5-diyl; substituted imidazolin-2-onyl groups such as 4-(4-fluorophenyl)-1-methyl-3-phenylimidazolin-2-on-5-yl; substituted vinyl groups such as 2,2-diphenylethenyl, 1-isopropyl-2,2-bis(4- fluorophenyl)ethenyl, 1-(1-methyl-1H-tetrazol-5-yl)-2,2-(4-fluorophenyl)ethenyl. Especially, 2,4-dimethyl-6-(4-fluoro-3-methylphenyl)phenyl, 2-cyclopropyl-4-(4-fluorophenyl)quinolin-3-yl, and 1-isopropyl-2,2-bis(4-fluorophenyl)ethenyl are preferable because of the high potential of the corresponding optically active lactones.

The example of Ar in the above formulae includes condensed aromatic groups such as naphthyl group, anthryl group, and phenanthryl group. Especially, 1-naphthyl group, 2-naphthyl group, 1-anthryl group, and 2-phenanthryl group are preferable because of effective face blocking in the hydride reduction.

The optically active ester of β,δ-diketocarboxylic acid of the formula (II) or its enantiomer is prepared by condensing the optically active ester of acetoacetic acid or its enantiomer represented by the formula (VI) with the N-methoxyamide represented by the formula (VII).

The optically active ester of acetoacetic acid of the formula (VI) or its enantiomer is easily prepared by ester-exchange of methyl or ethyl acetoacetate with an alcohol represented by the following formula (VIII):

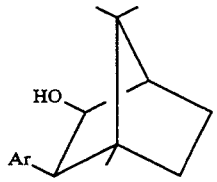

(VIII)

wherein Ar is a condensed aromatic group, or the enantiomer; or by contacting the alcohol of the formula (VIII) or the enantiomer with diketene.

The enantiomer of the compound (VIII) where Ar is 1-naphthyl is obtained from easily available (+)-camphor and 1-naphthylmagnesium bromide as reported in *J. Org. Chem.*, 52, 28(1987). According to the same procedure, the alcohol of the formula (VIII) itself is also obtainable from (−)-camphor as shown in Referential Example 1.

The ester-exchange for preparing the optically active ester of the formula (VI) is successfully conducted by heating a mixture of the acetoacetate and the alcohol of the formula (VIII) or its enantiomer in a molar ratio of 1:1 to 1:5. Solvent can be optionally used and the examples include benzene, toluene, xylene, and dioxane. The reaction conveniently proceeds at a temperature between room temperature and a boiling point of the solvent used. The reaction is further accelerated by adding an amine-type base, e.g., 4-dimethylaminopyridine, 4-(1-pyrrolidino)pyridine or pyridine, as a catalyst. The amount of the catalyst to be added ranges from so-called catalytic amount to 1 molar equivalent.

The reaction of the alcohol of the formula (VIII) with diketene is conducted under the well-known conditions.

The N-methoxyamide of the formula (VII) is attainable according to a conventional method which comprises converting the corresponding carboxylic acid into acid chloride followed by treating the chloride with N,O-dialkylhydroxylamine such as N,O-dimethylhydroxylamine as described in Japanese Patent Application Laying Open (KOKAI) No. 165547/89.

The optically active ester of β,δ-diketocarboxylic acid of the formula (II) or its enantiomer is prepared by treating the above optically active acetoacetate of the formula (VI) with one or more bases, followed by condensing resulting dianion with the N-methoxyamide of the formula (VII) according to a known method described in Japanese Patent Application Laying Open (KOKAI) No. 165547/89. The examples of the bases include lithium diisopropylamide, sodium hexamethyldisilazide, butyllithium, s-butyllithium, and t-butyllithium, as well as combination of sodium hydride and one of the above bases. Thus, the compound (VII) is treated with 0.9 to 1.3 molar equivalents of sodium hydride and 0.9 to 1.3 molar equivalents of lithium diisopropylamide or butyllithium at preferably −78° C. to room temperature to give corresponding dianion, which was then treated with 0.5 to 2 molar equivalents of the N-methoxyamide of the formula (VII) at −78° C. to room temperature. In these reactions, it is convenient to employ a solvent such as diethyl ether, tetrahydrofuran (THF), toluene, hexamethylphosphoric triamide, N,N'-dimethylpropyleneurea or combination thereof.

The stereoselective reduction of the optically active ester of β,δ-diketocarboxylic acid of the formula (II) or its enantiomer into the optically active ester of β,δ-syn-dihydroxycarboxylic acid of the formula (IV) or its enantiomer is achieved by the action of sodium borohydride in the presence of an organoboron compound represented by the formula: $R^5_2BZ^2$ where $R^5$ is a straight or branched alkyl group of 2 to 8 carbon atoms and $Z^2$ is a halogen atom or an alkoxy group having 1 to 8 carbon atoms. The examples of the organic boron compounds include diethylmethoxyborane, dibutylmethoxyborane, diisobutylmethoxyborane, diethylethoxyborane, diethylchloroborane, and diethylbromoborane. The reaction can be conducted in a protic solvent such as methanol, ethanol, or isopropyl alcohol at a temperature between −100° C. and a boiling point of the solvent, preferably between −78° C. and room temperature. Optionally, other inert solvents such as THF, diethyl ether, dichloromethane, and toluene may be used as a mixture with methanol. The amount of the organoboron compound to be used ranges from equimolar to five molar equivalents, preferably 1.0 to 2.5 molar equivalents relative to the substrate (II). The amount of sodium borohydride may be in the range of from equimolar to large excess, preferably from 1 to 6 molar equivalents in view of the cost, relative to the substrate (II).

The optically active enantio-ester of β,δ-syn-dihydroxycarboxylic acid of the formula (V) or its enantiomer is prepared by the action of sodium borohydride in the presence of an organoboron compound represented by the formula: $Me_2BZ^3$ where $Z^3$ is a halogen atom or an alkoxy group having 1 to 8 carbon atoms, following a procedure similar to the above selective reduction into the optically active ester of β,δ-syn-dihydrocarboxylic acid of the formula (IV) or its enantiomer. The preferable examples of the organic boron compounds include dimethylhaloboranes, especially dimethylbromoborane, and dimethylalkoxyborane such as dimethylethoxyborane. The reduction proceeds stepwise. In view of the enolization of the carbonyl group of the β,δ-diketocarboxylic acid ester of the formula (II), it is reasonable that the optically active ester of β,δ-syn-dihydroxycarboxylic acid of the formula (IV) or its enantiomer is formed via the optically active ester of hydroxyketocarboxylic acid of the formula (III) or its enantiomer, and the optically active enantio-ester of β,δ-syn-dihydroxycarboxylic acid of the formula (V') or its enantiomer via the optically active enantio-ester of hydroxyketocarboxylic acid represented by the following formula (III'):

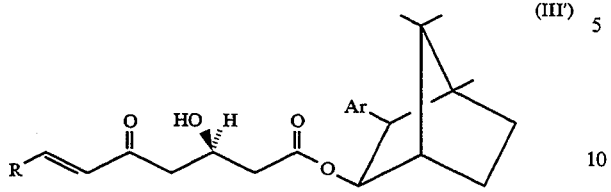

wherein R and Ar are the same as above, or its enantiomer.

Alternatively, the optically active ester of β,δ-syn-dihydroxycarboxylic acid of the formula (IV) or its enantiomer is prepared by reducing the optically active ester of β,δ-diketocarboxylic acid of the formula (II) or its enantiomer to form the optically active ester of β-hydroxy-δ-ketocarboxylic acid of the formula (III) or its enantiomer (first stereoselective reduction), followed by further reduction of the resulting β-hydroxy-δ-ketocarboxylic acid ester (second stereoselective reduction).

The first reduction is effected by employing an organoaluminium compound represented by the formula: $HAlR^3_2$ as a reducing agent, wherein $R^3$ is ethyl, propyl, butyl, isobutyl, or octyl group. The amount of the organoaluminium compound may range from 1.8 to 10 molar equivalents, preferably 2 to 3 molar equivalents in view of the cost, relative to the substrate (II). The reaction is conducted in an aprotic solvent such as diethyl ether, THF, benzene, toluene, hexane or dichloromethane at a temperature of from −150° C. to the boiling point of the solvent used. The preferred reaction temperature may depend on the particular substrate and is preferably between −100° C. to room temperature.

The second reduction is achieved by the action of sodium borohydride in the presence of an organoboron compound represented by the formula: $R^4_2BZ^1$, where $R^4$ is a straight or branched alkyl group of 1 to 8 carbon atoms and $Z^1$ is a halogen atom or an alkoxy group having 1 to 8 carbon atoms, under similar conditions as described above at the reduction of the ester of β,δ-diketocarboxylic acid of the formula (II) into the same product (IV). The preferable amount of sodium borohydride ranges from 1.0 to 6.0 molar equivalents.

EXAMPLES

The present invention is further illustrated in detail with reference to the following examples. It should be understood that the present invention is not limited to those examples.

REFERENTIAL EXAMPLE 1

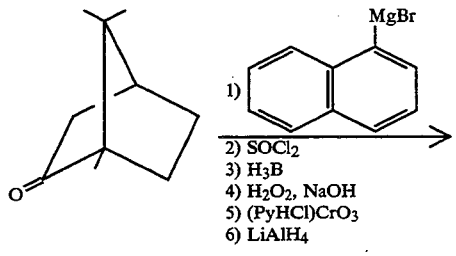

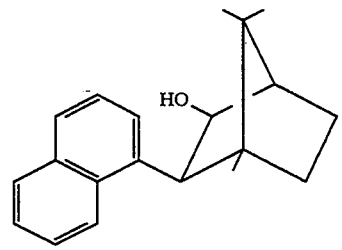

A THF (100 ml) solution of 1-bromonaphthalene (46 ml, 0.335 mol) was slowly added dropwise to a THF (200 ml) suspension of metallic magnesium ribbon (9.5 g, 0.39 mol) under argon atmosphere, and the whole was stirred at room temperature for 1 hour and at refluxing temperature of THF for 1 hour.

The resulting THF solution of 1-naphthylmagnesium bromide was cooled to room temperature. Then, a THF (200 ml) solution of (−)-camphor (50 g, 0.328 mol) was added thereto, and the whole was heated under reflux for 72 hours. The reaction was terminated by cooling with ice-water and adding saturated ammonium chloride aq solution. Then, the organic layer was filtered off, and the solid residue was treated with 10% hydrochloric acid and extracted with diethyl ether. The combined organic layer was dried over anhydrous magnesium sulfate and, after filtration, concentrated to give 121 g of a crude (1S)-2-(1-naphthyl)-1,7,7-trimethylbicyclo [2.2.1]-heptan-2-ol as an oil.

To the resulting crude product dissolved in pyridine (150 ml) was added thionyl chloride (12 ml) rapidly under ice cooling, and the whole was further stirred for 1.5 hours. Water (150 ml) was added thereto, and the reaction mixture was extracted with hexane (100 ml×3 times). The hexane extract was washed successively with 10% hydrochloric acid, saturated copper sulfate aq solution, saturated sodium hydrogen carbonate aq solution, and saturated sodium chloride aq solution, dried over anhydrous magnesium sulfate, and finally concentrated in vacuo. Removal of remaining camphor and naphthalene from the residue at 110° C. under 0.1 Torr afforded 57.5 g (67% yield) of (1S)-2-(1-naphthyl)-1,7,7-trimethyl-2-bicyclo[2.2.1]heptene.

The olefin was dissolved in toluene (100 ml), and borandimethyl sulfide complex (24 g, 30 ml, 0.316 mol) was added thereto. The mixture was refluxed for 5 hours and stirred at room temperature overnight, then cooled to 0° C. Thereto were added dropwise 50% sodium hydroxide aq solution (75 ml), ethanol (50 ml) and 30% hydrogen peroxide (60 ml), successively. After stirring at room temperature for 1 hour, the organic layer was separated, and the aqueous layer was extracted with dichloromethane (50 ml×twice). The combined organic layer was dried over anhydrous magnesium sulfate and concentrated in vacuo. The resulting solid residue was dissolved in hexane (150 ml), and the solution was allowed to stand at −78° C. to afford 14.9 g (24% yield) of (4R)-4,7,7-trimethyl-3-exo-(1-naphthyl)bicyclo[2.2.1]heptan-2-endo-ol as pale gray solids. $R_f$=0.17 (ethyl acetate:hexane=1:9) IR (KBr): 3600, 3450, 2995, 2900, 1605, 1515, 1455, 1395, 1290, 1155, 1060, 1040, 800, 780 cm$^{-1}$.

$^1$H NMR (CDCl$_3$): δ=0.52 (s, 3H), 0.90 (s, 3H), 1.03 (s, 3H), 1.10–2.36 (m, 5H), 3.36 (d, J=6 Hz, 1H), 5.00–5.26 (br, 1H), 7.30–8.17 (m, 7H).

A dichloromethane (30 ml) solution of the above alcohol (13.4 g, 48 mmol) was added to a mixture of pyridinium chlorochromate (25.8 g, 120 mmol), sodium acetate (15.7 g, 192 mmol) and dichloromethane (270 ml), and the whole was stirred at room temperature for 3 hours. After adding Celite (20 g), the mixture was filtered through a Celite layer (50 g) to remove insoluble substances. The Celite layer was washed with diethyl ether (50 ml × twice) and acetone (50 ml) successively, and the combined filtrate was dried over anhydrous magnesium sulfate and then concentrated in vacuo. The crude product was purified by column chromatography (silica gel 120 g, ethyl acetate:hexane=5:95) to give 12.8 g of (4R)-3-exo(1-naphthyl)-4,7,7-trimethyl-2-bicyclo[2.2.1]heptan-2-one as solids. Recrystallization from ethyl acetate-dichloromethane (5:1) afforded 10.8 g (81% yield) of pure product. mp=203°–205° C. $R_f$=0.25 (ethyl acetate:hexane=5:95) $[\alpha]_D^{20}$= −190.31° (c 0.44, CHCl$_3$) IR (KBr): 3000, 2970, 2895, 1745, 1600, 1495, 1460, 1400, 1380, 1300, 1160, 1100, 800, 780 cm$^{-1}$.

$^1$H NMR (CDCl$_3$): δ=0.80 (s, 3H), 0.96 (s, 3H), 1.13 (s, 3H), 1.53–2.46 (m, 5H), 4.13 (s, 1H), 7.33–8.00 (m, 7H). MS:m/z (rel. intensity) 278 (M$^+$, 8), 181 (9), 169 (13), 168 (100), 165 (12), 140 (16), 137 (7), 109 (6), 69 (5), 55 (8), 53 (5), 41 (30).

The resulting ketone (2.76 g, 10 mmol) dissolved in THF (5 ml) was added slowly to lithium aluminium hydride (0.40 g, 10.5 mmol) suspended in THF (20 ml), and the whole was stirred at room temperature for 1 hour. The reaction was quenched by cooling the mixture to 0° C. and by adding water (0.5 ml), 10% sodium hydroxide aq solution (0.5 ml), and water (2 ml), successively. After stirring at room temperature for 30 minutes, the mixture was filtered to remove insoluble substances. The residue was washed with diethyl ether and acetone. The combined organic layer was dried over anhydrous magnesium sulfate and then concentrated. The resulting crude product (2.3 g) was purified by recrystallization from ethanol (8 ml)-water (1.5 ml) to give 1.75 g (63% yield) of (4R)-3-exo-(1-naphthyl)-4,7,7-trimethylbicyclo[2.2.1 ]heptan-2-exo-ol. mp=151°–152° C. $R_f$=0.36 (ethyl acetate:hexane=1:9) $[\alpha]_D^{20}$= +179.88° (c 0.70, CHCl$_3$) IR (KBr): 3610, 3540, 2980, 2910, 1605, 1515, 1490, 1460, 1400, 1100, 1065, 1045, 800 cm$^{-1}$.

$^1H$ NMR (CDCl$_3$): δ=0.83–2.06 (br m, 5H), 1.00 (s, 3H), 1.23(s, 3H), 1.40 (s, 3H), 3.95 (d, J=8 Hz, 1H), 4.48 (d, J=8 Hz, 1H), 7.36–8.37 (br m, 7H). MS:m/z (rel. intensity) 280 (M$^+$, 6), 171 (13), 170 (100), 169 (13), 165 (11), 142 (21), 141 (20), 41 (14).

REFERENTIAL EXAMPLE 2

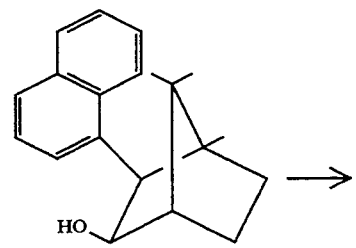

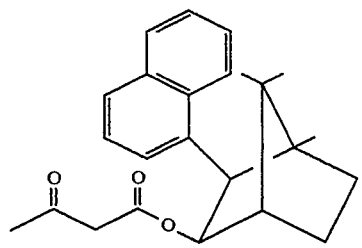

Methyl acetoacetate (1.51 g, 13.0 mmol) was added to a mixture of (4S)-4,7,7-trimethyl-3-exo-(1-naphthyl)-bicyclo[2.2.1]heptan-2-exo-ol (1.20 g, 4.3 mmol), 4-dimethylaminopyridine (0.24 g, 2.0 mmol) and toluene (20 ml) under argon atmosphere, and the whole was heated under reflux for 36 hours After cooling to 0° C. the mixture was diluted with saturated ammonium chloride aq solution and extracted with diethyl ether (100 ml). The ethereal layer was washed with water (30 ml) twice and dried over anhydrous magnesium sulfate. After concentration, the resulting crude product (2.60 g) was purified by a column chromatography (silica gel, ethyl acetate:hexane=1:9) to give 1.54 g (98% yield) of (4S)-4,7,7-trimethyl-3-exo-(1-naphthyl)bicyclo [2.2.1 ]heptan-2-exo-yl acetoacetate as a colorless oil. $R_f$=0.24 (hexane:ethyl acetate=10:1) $[\alpha]_D^{20}$= −132.8° (C 0.53, CHCl$_3$) $^1$H NMR (CDCl$_3$): δ=1.01 (s, 3H), 1.25 (s, 3H), 1.28 (s, 3H), 1.4–2.1 (m, 8H), 2.60 (s, 2H), 4.10 (d, J=8.9 Hz, 1H), 5.61 (d, J=8.8 Hz, 1H), 7.3–8.04 (m, 7H). IR (neat): 2970, 1755, 1725, 1555, 1400, 1245, 1035 cm$^{-1}$. MS:m/z (rel. intensity) 364 (M$^+$, trace), 282 (12), 171 (13), 170 (100), 169 (13), 168 (11), 165 (11), 142 (35), 141 (23), 139 (10), 95 (12).

EXAMPLE 1

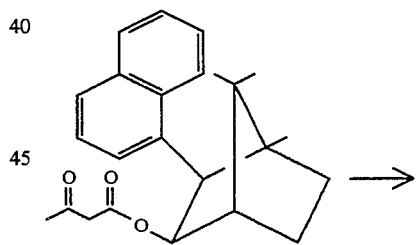

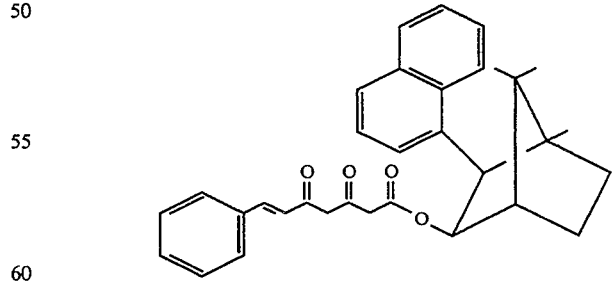

The acetoacetate (1.46 g, 4.0 mmol) obtained in Referential Example 2 was added at 0° C. to a THF (25 ml) suspension of sodium hydride (0.16 g, content 60%, oil dispersion, 4 mmol), and the whole as stirred for 15 minutes and then cooled to −15° C. Butyllithium (1.60M hexane solution, 2.5 ml, 4.0 mmol) was slowly added thereto dropwise, and the mixture was stirred at −15° C. for 20 minutes and ten cooled at −78° C. THF (1 ml) solution of N-methoxy-N-methylcinnamamide (0.76 g, 4.0 mmol) was slowly added thereto, and the whole as stirred at −78° C. for 1 hour and at room temperature overnight. Then, dil. hydrochloric acid (ca. 1 ml) as added to terminate the reaction, and the whole as diluted with ethyl acetate (ca. 30 ml). The organic layer as washed with saturated sodium chloride aq solution (ca. 10) and then dried over anhydrous magnesium sulfate. Concentration of the organic layer afforded 1.89 g of a crude product which as purified by column chromatography (silica gel, dichloromethane) to give 0.51 g (26% yield) of (4S)-4,7,7-triethyl-3-exo-(1-naphthyl)bicyclo[2.2.1]heptan-2-exo-yl (E)-7-phenyl-3,5-dioxo-6-heptenoate. $R_f$=0.48 (hexane:dichloromethane=1:1) $[\alpha]_D^{20}$=−141.0° (c 1.90, CHCl$_3$)

$^H$NMR (CDCl$_3$): δ=1.00 (s, 3H), 1.21 (s, 3H), 1.29 (s, 3H), 1.42–1.60 (m, 2H), 1.80–1.72 (m, 1H), 1.91–2.20 (m, 2H), 2.60 (d, J=15.0 Hz, 1H), 2.66 (d, J=15.0 Hz, 1H), 4.06 (d, J=8.5 Hz, 1H), 4.78 (s, 1H), 5.56 (d, J=8.5 Hz, 1H), 6.24 (d, J=16.0 Hz, 1H), 7.73 (dd, J=15.5, 7.5 Hz, 1H), 7.40–7.50 (m, 7H), 7.56 (dd, J=6.5, 1.0 Hz, 1H), 7.60 (d, J=7.5 Hz, 1H), 7.66 (d, J=8.5 Hz, 1H), 7.77 (dd, J=8.0, 1.0 Hz, 1H), 8.02 (d, J=8.5 Hz, 1H), 14.48 (br s, 1H). IR (CHCl$_3$): 3060, 2950, 1735, 1640, 1590, 1320, 1160, 1120, 1020, 985 cm$^{-1}$. MS:m/z (rel. intensity) 494 (M+, 3), 263 (5), 247 (6), 215 (19), 179 (13), 173 (49), 171 (16), 170 (100), 165 (23), 152 (9), 142 (12), 141 (39), 131 (48), 121 (12), 115 (20), 103 (32), 93 (23), 84 (22), 69 (26), 67 (14), 55 (25), 51 (15), 47 (13), 43 (31).

These data shows that the diketoester exists in an enol form represented by the following formula:

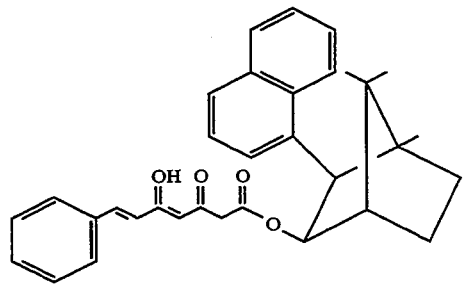

EXAMPLE 2

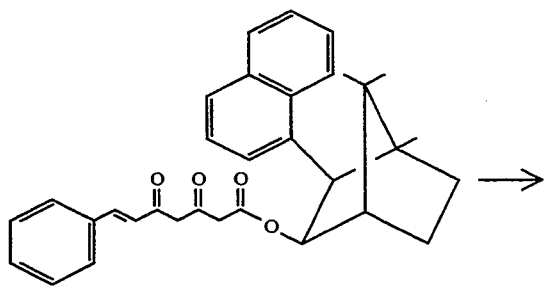

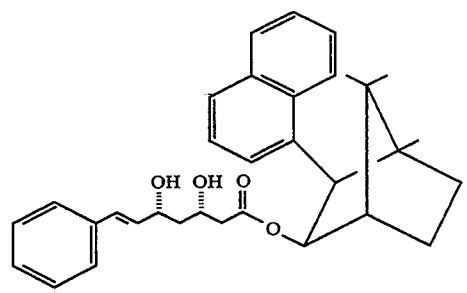

The optically active diketocarboxylic acid ester (66 mg, 0.134 mmol) obtained in Example 1 was dissolved in a solvent mixture of THF (1 ml) and methanol (0.25 ml). Then, diethylmethoxyborane (15 mg, 0.15 mmol) was added thereto at −78° C. under argon atmosphere. The mixture was once warmed to room temperature and then cooled again to −78° C. Thereto was added sodium borohydride (26 mg, 0.67 mmol). After stirring at −78° C. for 3 hours and at room temperature overnight, the mixture was treated with acetic acid (3 ml) to terminate the reaction, diluted with ethyl acetate (ca. 10 ml), washed with 5% sodium hydrogen carbonate aq solution (ca. 10 ml) and then dried over anhydrous magnesium sulfate. The organic layer was concentrated in vacuo to give a crude product. Methanol (30 ml) was added to the product and then removed in vacuo. This operation was repeated 10 times to decompose and evaporate organoboron compound. The resulting crude product (51 mg) was purified by thin layer chromatography (silica gel, ethyl acetate:hexane=3:7) to give 37 mg (57% yield) of (4S)-4,7,7-trimethyl-3-exo-(1-naphthyl)bicyclo[2.2.1]heptan-2-exo-yl (3S, 5R)-7-phenyl-3,5-dihydroxy-6-heptenoate. HPLC analysis (silica gel 60) of the product showed that it was an isomeric mixture in a ratio of 4.5:1. Main component was separated by liquid chromatography. $R_f$=0.27 (hexane:ethyl acetate=2:1) IR (CHCl$_3$): 3550, 2950, 1730, 1600, 1395, 1250, 1180, 1085, 1015, 965, 785 cm$^{-1}$.

$^1$H NMR (CDCl$_3$): δ=1.01 (s, 3H), 1.26 (s, 3H), 1.33 (s, 3H), 0.84–2.18 (br m, 11H), 3.07–3.13 (m, 1H), 4.08 (d, J =8.8 Hz, 1H), 4.13–4.18 (m, 1H), 5.53 (s, J=8.8 Hz, 1H), 6.00 (dd, J=6.18, 15.9 Hz, 1H), 6.51 (d, J=15.9 Hz, 1H), 7.21–7.52 (m, 8H), 7.66 (d, J=7.4 Hz, 1H), 7.73 (d, J=8.2 Hz, 1H), 7.84 (d, J=8.2 Hz, 1H), 8.05 (d, J=8.5 Hz, 1H). MS:m/z (rel. intensity) 498 (M+, weak), 480 (weak), 463 (weak), 264 (19), 263 (79), 262 (13), 235 (34), 207 (32), 201 (21), 170 (100), 155 (39), 141 (84), 131 (42), 115 (33), 104 (16), 95 (19), 91 (33), 71 (28), 55 (24), 43 (27).

REFERENTIAL EXAMPLE 3

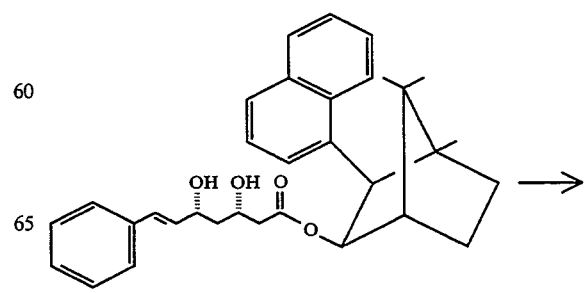

-continued

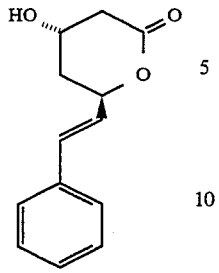

Aqueous 1M sodium hydroxide solution (60 μl, 0.06 mmol) was added to a methanol (0.5 ml) solution of the dihydroxyester (18 mg, 0.036 mmol) obtained in Example 2. The mixture was stirred at room temperature for 36 hours, diluted with water, and extracted with diethyl ether to remove neutral substances. The aqueous layer was acidified by adding 5M hydrochloric acid and then extracted with diethyl ether (10 ml×3 times). The ethereal layer was washed with saturated sodium chloride aq solution and then dried over anhydrous magnesium sulfate. The organic layer was concentrated in vacuo to give 8 mg of a corresponding carboxylic acid which was subsequently dissolved in toluene (2 ml). The solution was heated under reflux for 9 hours under argon atmosphere. After removing the toluene in vacuo, the residue was purified by thin layer chromatography to give 6.1 mg (76% yield) of (3S, 5R)-3,5-dihydroxy-7-phenyl-6-hepten-1,5-olide. HPLC analysis (CHIRAL OA, hexane:isopropyl alcohol=9:1) of the product showed that its optical purity was 94% ee. $R_f$=0.24 (dichloromethane:acetone=9:1) $[\alpha]_D^{20}$= −11.33° (c 0.41, CHCl₃)

¹H NMR (CDCl₃): δ=1.94–2.01 (m, 1H), 2.09–2.15 (m, 1H), 2.65–2.71 (m, 1H), 2.81 (dd, J=5.0, 17.8 Hz, 1H), 4.45 (quint, J=3.9 Hz, 1H), 5.37 (dddd, J=1.1, 3.5, 6.0, 11.0 Hz, 1H), 6.21 (dd, J=6.0, 15.9 Hz, 1H), 6.71 (dd, J=0.9, 15.9 Hz, 1H), 7.24–7.45 (m, 5H). MS:m/z (rel. intensity) 218 (M⁺, 15), 200 (13), 172 (10), 131 (21), 130 (20), 129 (24), 114 (21), 104 (100), 91 (40), 77 (21), 68 (34), 51 (15), 43 (32). IR (KBr): 3440, 3080, 3050, 2975, 2940, 1725, 1600, 1500 1425, 1395, 1375, 1245, 1165, 1075, 1035, 980, 755, 695 cm⁻¹.

EXAMPLE 3

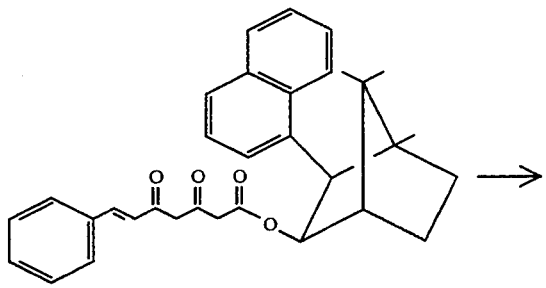

-continued

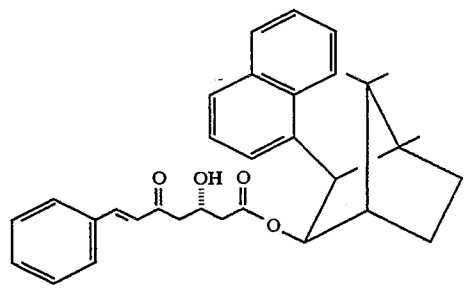

The β,δ-diketocarboxylic acid ester (33 mg, 0.067 mmol) obtained in Example 1 was dissolved in THF (1 ml). Diisobutylaluminium hydride (DIBAL) (0.97M toluene solution, 0.153 ml, 0.148 mmol) was added thereto at −78° C. under argon atmosphere, and the whole was stirred at −78° C. for 4 hours. To the mixture was added 1M hydrochloric acid to terminate the reaction and hydrolize the aluminium alkoxides at the same time. The resulting mixture was extracted with ethyl acetate (50 ml), and the organic layer was washed with 5% sodium hydrogen carbonate aq solution, dried over anhydrous magnesium sulfate and then concentrated in vacuo. The crude product (34 mg) was purified by thin layer chromatography (silica gel, ethyl acetate:-hexane=4:6) to give 28 mg (85% yield) of (4S)-4,7,7-trimethyl-3-exo-(1-naphthyl)bicyclo[2.2.1]heptan-2-exo-yl (3S, 6E)-3-hydroxy-5-oxo-7-phenyl-6-heptenoate. HPLC analysis (silica gel 60, hexane:ethanol=80:1) of the product showed that it was an isomeric mixture in a ratio of 95.3:4.7. $R_f$=0.49 (hexane:ethyl acetate=2:1) $[C]_D^{20}$= −99.17° (C 1.45, CHCl₃)

¹H NMR (CDCl₃): δ=1.00 (s, 3H), 1.25 (s, 3H), 1.35 (s, 3H), 1.54–2.17 (m, 10H), 3.54–3.61 (m, 1H), 4.09 (d, J= 8.7 Hz, 1H), 5.56 (d, J=8.7 Hz, 1H), 6.53 (J=16 Hz, 1H), 7.37–7.6 (m, 13H). IR (CHCl₃): 3580, 2950, 2925, 1725, 1680, 1650, 1605, 1390, 1120, 1090, 780 cm⁻¹. MS:m/z (rel. intensity) 496 (M⁺, 1), 478 (2), 350 (8), 262 (12), 240 (26), 199 (17), 179 (10), 171 (14), 170 (100), 169 (10), 165 (16), 146 (17), 145 (12), 141 (28), 131 (53), 103 (27), 77 (19), 71 (14), 55 (10), 43 (28).

EXAMPLE 4

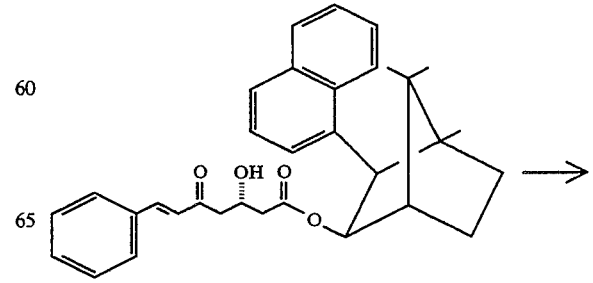

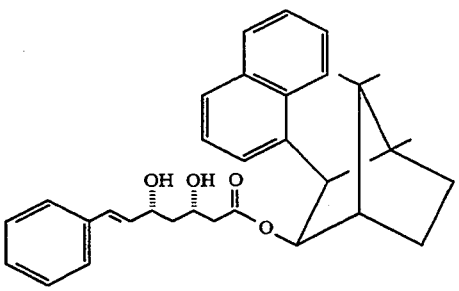

The β-hydroxy-δ-ketocarboxylic acid ester (15 mg, 0.03 mmol) obtained in Example 3 was dissolved in a solvent mixture of THF (0.5 ml) and methanol (0.1 ml). Diethylmethoxyborane (4.3 μl, 0.031 mmol) was added thereto at −78° C. under argon atmosphere. The mixture was stirred at room temperature for 15 minutes and cooled again at −78° C. Sodium borohydride (3.8 mg, 0.10 mmol) was added thereto. The mixture was stirred at −78° C. for 7 hours and at room temperature for 8 hours, treated with acetic acid (1 ml), diluted with ethyl acetate, and washed successively with 5% sodium hydrogen carbonate aq solution and saturated sodium chloride aq solution. The organic layer was dried over anhydrous magnesium sulfate and then concentrated in vacuo to give 16 mg of a crude product. The crude product was purified by thin layer chromatography to give 12 mg (80% yield) of (4S)-4,7,7-trimethyl-3-exo-(1-naphthyl)bicyclo[2.2.1]heptan-2-exo-yl (3S, 5R, 6E)-7-phenyl-3,5-dihydroxy-6-heptenoate. HPLC analysis (silica gel 60, hexane:ethanol=40:1) of the product confirmed that it was composed of a single component. The spectral data of the product were identical with those of the main product obtained in Example 2. $R_f$=0.28 (hexane:ethyl acetate=2:1) $[\alpha]_D^{20}$= −86.5° (c 0.55, CHCl$_3$)

REFERENTIAL EXAMPLE 4

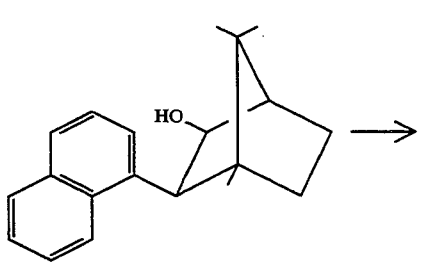

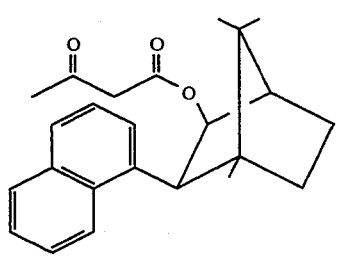

In a way similar to Referential Example 2, an acetoacetate, (4R)-4,7,7-trimethyl-3-exo-(1-naphthyl)bicyclo[2.2.1]heptan-2-exo-yl acetoacetate was prepared from (4R)-4,7,7-trimethyl-3-exo-(1-naphthyl)bicyclo[2.2.1]heptan-2-exo-ol obtained in Referential Example 1, in 81% yield. $R_f$=0.25 (hexane:ethyl acetate=10:1) $[\alpha]_D^{20}$= +130.55° (c 0.80, CHCl$_3$)

The other spectral data of the product were identical with those of the product obtained in Referential Example 2.

EXAMPLE 5

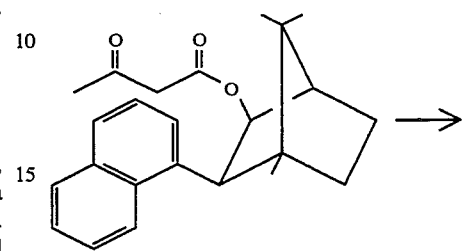

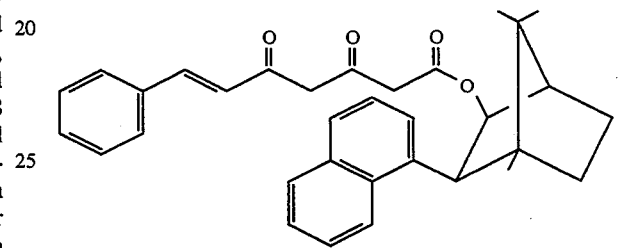

Following the procedure of Example 1, (4R)-4,7,7-trimethyl-3-exo-(1-naphthyl)bicyclo[2.2.1]heptan-2-exo-yl 7-phenyl-3,5-dioxo-6-heptenoate was prepared from the optically active acetoacetate obtained in Referential Example 4, in 26% yield. $R_f$=0.47 (hexane:dichloromethane=1:1) $[\alpha]_D^{20}$= +102.35° (c 0.68, CHCl$_3$)

The other spectral data of the product were identical with those of the product obtained in Example 1.

EXAMPLE 6

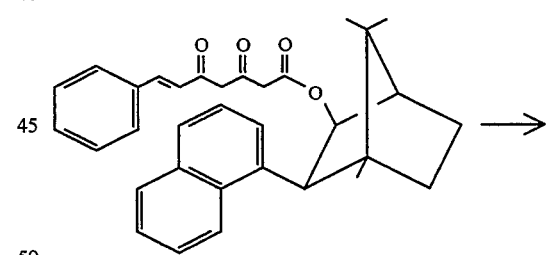

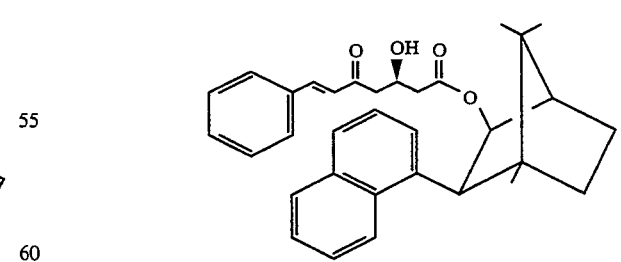

DIBAL (0.97M toluene solution, 0.113 ml, 0.11 mmol) was added at −78° C. under argon atmosphere to a THF (1 ml) solution of the optically active β,δ-diketocarboxylic acid ester (25 mg, 0.05 mmol) obtained in Example 5, and the whole was stirred at −78° C. for 4 hours. Workup and purification similar to those in Example 3 afforded 17.6 mg (70% yield) of (4R)-4,7,7- trimethyl-3-exo-(1-naphthyl)bicyclo[2.2.1]heptan-2-exo-yl (3R, 6E)-3-hydroxy-5-oxo-7-phenyl-6-heptenoate. $R_f$=0.49 (hexane:ethyl acetate=2:1) $[\alpha]_D^{20}$= +103.7° (c 0.96, CHCl₃)

HPLC analysis (silica gel 60) of the product showed a diastereomeric ratio of >95:5. The other spectral data of the product were identical with those of the product obtained in Example 3.

EXAMPLE 7

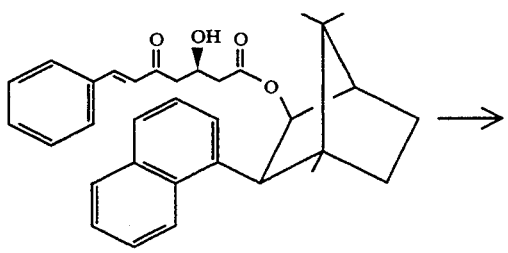

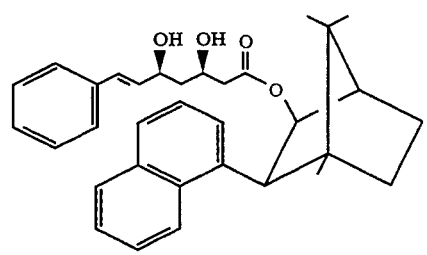

The optically active β-hydroxy-δ-ketocarboxylic acid ester (10 mg, 0.02 mmol) obtained in Example 6 was dissolved in a mixture of THF (1 ml) and methanol (0.1 ml). Then, diethylmethoxyborane (4 μl , 0.03 mmol) was added thereto at −78° C. under argon atmosphere. The mixture was stirred at room temperature for 15 minutes and cooled again at −78° C. Sodium borohydride (4 mg, 0.11 mmol) was added thereto, and the whole was stirred at −78° C. for 3 hours and at room temperature for 10 hours. Workup and purification afforded 7.8 mg (78% yield) of (4R)-4,7,7-trimethyl-3-exo-(1-naphthyl)bicyclo[2.2.1]heptan-2-exo-yl (3R,5S,6E)-3,5-dihydroxy-7-phenyl-6-heptenoate.

HPLC analysis (silica gel 60) of the product confirmed that it was composed of a single component. $R_f$=0.29 (hexane:ethyl acetate=2:1) $[\alpha]_D^{20}$= +84.54° (c 0.44, CHCl₃)

The other spectral data of the product were identical with those of the product obtained in Example 4.

REFERENTIAL EXAMPLE 5

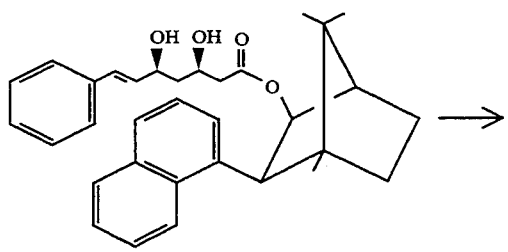

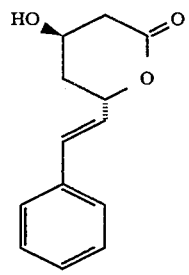

Aqueous 1M sodium hydroxide solution (60 μl, 0.06 mmol) was added to a methanol (2 ml) solution of the optically active β,δ-syn-dihydroxycarboxylic acid ester (8 mg, 0.016 mmol) obtained in Example 7 and the whole was stirred at room temperature for 51 hours. Workup and purification similar to those in Referential Example 3 afforded 2 mg (56% yield) of (3R, 5S)-3,5-dihydroxy-7-phenyl-6-hepten-1,5-olide. $R_f$=0.24 (dichloromethane:acetone=10:1) $[\alpha]_D^{20}$= +10.66° (c 0.15, CHCl₃)

HPLC analysis (CHIRAL OA, hexane:isopropyl alcohol=9:1) of the product showed that its diastereomer ratio was ca. 99:1 and the optical purity was at least 97% ee. The spectral data of the product were completely identical with those of the product obtained in Referential Example 3.

REFERENTIAL EXAMPLE 6

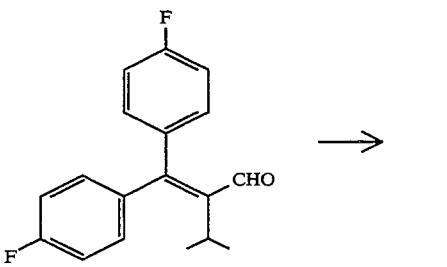

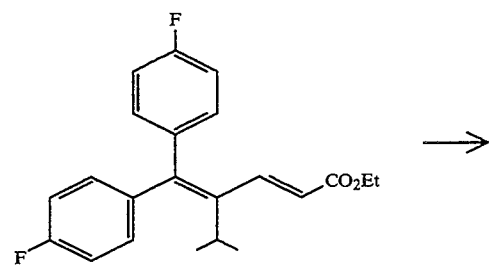

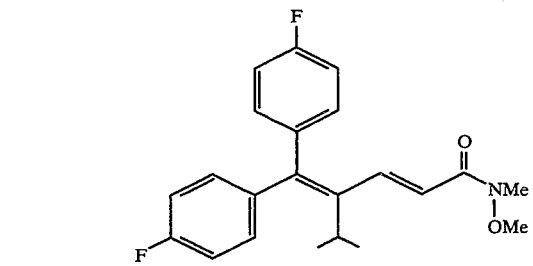

A THF (2.0 ml) solution of triethyl phosphonoacetate (EtO)₂P(O)CH₂COOEt (0.224 g, 0.198 ml, 1.00 mmol) was added at 0° C. under argon atmosphere to sodium hydride (content 60%, oil dispersion, 42 mg, 1.04 mmol)

which had been washed with hexane, and the mixture was stirred for 30 minutes. To the mixture was added a THF (1 ml) solution of 3-methyl-2-bis(4-fluorophenyl)-methylidenbutanal (0.286 g, 1.0 mmol) prepared according to the method described in Tetrahedron Lett., 29, 929 (1988). After stirring at room temperature overnight, the mixture was then diluted with water (25 ml) and extracted with hexane (30 ml×3 times). The organic layer was washed with water (30 ml×twice) and saturated sodium chloride aq solution and finally dried over anhydrous magnesium sulfate. Concentration in vacuo followed by purification by thin layer chromatography (silica gel, ethyl acetate:hexane=1:9) to give 0.28 g (79% yield) of ethyl (E)-5-methyl-4-bis(4-fluorophenyl)methylidene-2-hexenoate. mp=66°-67° C. $R_f$=0.49 (ethyl acetate:hexane=1:10) IR (KBr): 3075, 3050, 3005, 1715, 1620, 1505, 1370, 1305, 1230, 1195, 1160, 1100, 1090, 1005, 875, 855, 840, 780, 585, 565 cm$^{-1}$.

$^1$H NMR (CDCl$_3$): δ=1.28 (d, J=7.5 Hz, 6H), 1.37 (t, J=8.0 Hz, 3H), 3.07-3.50 (m, 1H), 4.58 (q, J=8.0 Hz, 2H), 6.63 (d, J=18.0 Hz, 1H), 7.36-8.03 (m, 8H), 8.08 (d, J=18.0 Hz, 1H). MS:m/z (rel. intensity) 356 (M$^+$, 35), 283 (17), 282 (27), 268 (15), 267 (61), 256 (13), 252 (17), 251 (19), 208 (16), 241 (84), 240 (10), 239 (13), 238 (15), 227 (14), 221 (16), 220 (13), 203 (29), 201 (20), 153 (21), 133 (15), 125 (16), 123 (26), 109 (42), 43 (100).

A toluene (8 ml) solution of the above ester (2.38 g, 6.7 mmol) was added to powdery sodium hydroxide (0.34 g, 8.5 mmol) under argon atmosphere, and the whole was stirred at 60° C. for 5 hours. The reaction mixture was neutralized with 1M hydrochloric acid (10 ml) and extracted with ethyl acetate (25 ml×3 times). The organic layer was washed with water, saturated sodium chloride aq solution and then dried over anhydrous magnesium sulfate. Concentration of the organic layer in vacuo followed by recrystallization from a mixed solvent (hexane:ethyl acetate=4:1) gave 1.70 g (78% yield) of (E)-5-methyl-4-bis(4-fluorophenyl)methylidene-2-hexenoic acid. mp=225°-230° C. $R_f$=0.52 (hexane:ethyl acetate=1:1) IR (KBr): 3350, 2400, 3025, 1690, 1615, 1515, 1430, 1320, 1225, 1165, 1100, 1080, 1005, 965, 860, 850, 595, 580 cm$^{-1}$.

$^1$H NMR (CDCl$_3$): δ=1.20 (d, J=7.5 Hz, 6H), 2.73-3.20 (m, 1H), 6.03 (d, J=16.5 Hz, 1H), 6.73-7.36 (m, 8H), 7.45 (d, J=16.5 Hz, 1H). MS:m/z rel. intensity) 329 (M$^+$+1, 15), 328 (M$^+$, 68), 313 (34), 285 (23), 268 (20), 267 (82), 256 (43), 253 (18), 252 (27), 251 (30), 242 (19), 241 (98), 239 (23), 238 (27), 227 (21), 221 (25), 220 (21), 214 (13), 203 (48), 201 (42), 183 (17), 175 (20), 147 (20), 146 (19), 133 (31), 125 (27), 123 (46), 109 (74), 45 (17), 43 (100).

To the above carboxylic acid (1.70 g, 5.2 mmol) dissolved in benzene (15 ml) was added under argon atmosphere oxalyl chloride (1.27 g, 0.87 ml, 10.0 mmol) distilled right before use. After stirring at 60° C. for 2 hours, the solvent and excess oxalyl chloride were removed by evaporation at 60° C. under 20 Torr. To the residue dissolved in dichloromethane (25 ml) were added N,O-dimethoxyhydroxylamine hydrochloride (0.52 g, 5.34 mmol) and pyridine (0.85 g, 0.86 ml, 10.7 mmol), and the whole was stirred at room temperature overnight. The mixture was diluted with diethyl ether (100 ml), and the organic layer was washed with saturated ammonium chloride aq solution (100 ml×twice), dried over anhydrous magnesium sulfate, and concentrated in vacuo. The resulting crude product was purified by column chromatography (silica gel, ethyl acetate:hexane=3:7) to give 1.62 g (82% yield) of N-methyl-N-methoxy-(E)-5-methyl-4-bis (4-fluorophenyl)methylidene-2-hexenamide. mp=109°-110° C. $R_f$=0.48 (hexane:ethyl acetate=2:1) IR (KBr): 3200, 3005, 2960, 1660, 1610, 1515, 1420, 1390, 1235, 1170, 1105, 1070, 1005, 865, 850, 810, 590, 575 cm$^{-1}$.

$^1$H NMR (CDCl$_3$): δ=1.21 (d, J=7.5 Hz, 6H), 2.65-3.20 (m, 1H), 3.20 (s, 3H), 3.51 (s, 3H), 6.48 (d, J=16.5 Hz, 1H), 6.77-7.33 (m, 8H), 7.39 (d, J=16.5 Hz, 1H). MS:m/z (rel. intensity) 371 (M$^+$, 11), 312(22), 311 (100), 269 (14), 215 (22), 203 (14), 197 (14), 149 (16), 137 (18), 123 (26), 109 (57), 55 (16), 43 (48).

EXAMPLE 8

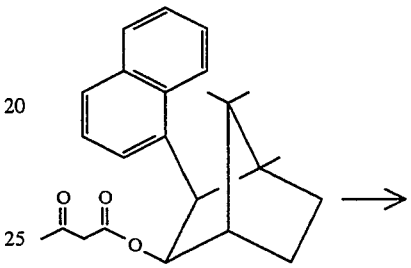

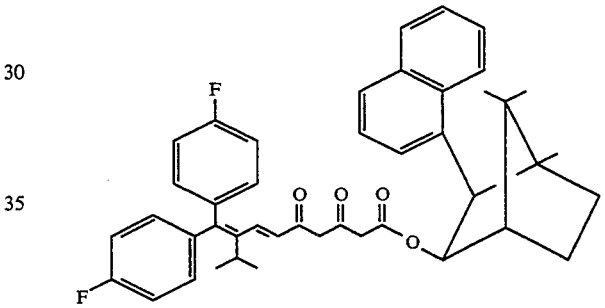

Sodium hydride (content 60%, oil dispersion, 104 mg, 2.5 mmol) was washed with hexane and suspended in THF under argon atmosphere. To the suspension was added at 0° C. a THF (2 ml) solution of the acetoacetate (0.91 g, 2.5 mmol) obtained in Referential Example 2, and the whole was stirred at 0° C. for 0.5 hours. The mixture was cooled at −10° C., and thereto was added butyllithium (1.52M hexane solution, 1.62 ml, 2.5 mmol) dropwise. The whole was stirred at −10° C. for 0.5 hours. The resulting dianion was treated with a THF (2 ml) solution of the amide (0.93 g, 2.5 mmol) obtained in Referential Example 6. After stirring at −10° C. for 2 hours and at room temperature overnight, the mixture was cooled to 0° C., treated with 1M hydrochloric acid (6 ml) to terminate the reaction and diluted with ethyl acetate (50 ml). The organic layer was washed with 5M sodium hydrogen carbonate aq solution (3 ml) and saturated sodium chloride aq solution and then dried over anhydrous magnesium sulfate. Removal of the solvent in vacuo afforded 1.91 g of a crude product which was purified by column chromatography to give 0.66 g (38% yield) of (4S)-4,7,7-trimethyl-3-exo-(1-naphthyl)-bicyclo[2.2.1]heptan-2-exo-yl (E)-9-methyl-8-bis(4-fluorophenyl)methylidene-3,5-dioxo-6-decenoate and 0.38 g (42%) of the starting acetoacetate recovered. The yield of the desired product was calculated to be 67% based on the starting material consumed. $R_f$=0.27 (hexane:dichloromethane=1:1) $[α]_D^{20}$=−116.230° (c 0.85, CHCl₃) IR (KBr): 3060, 2980, 2900, 1735, 1605, 1505, 1395, 1320, 1225, 1160, 1095, 1015, 835, 785 cm⁻¹.

¹H NMR (CDCl₃): δ=0.76-2.13 (m, 11H), 1.00 (s, 3H), 1.33 (s, 3H), 1.37 (s, 3H), 2.53 (s, 2H), 2.84-3.24 (m, 1H), 4.08 (d, J=9 Hz, 1H), 4.75 (s, 1H), 5.57 (d, J=9 Hz, 1H), 5.92 (d, J=16.5 Hz, 1H), 6.73-8.10 (m, 16H). MS:m/z (rel. intensity) 674 (M⁺, 2), 412 (4), 394 (13), 263 (14), 207 (11), 203 (14), 171 (14), 170 (100), 169 (14), 165 (13), 142 (20), 141 (26), 111 (28), 109 (12), 69 (27), 43 (22).

EXAMPLE 9

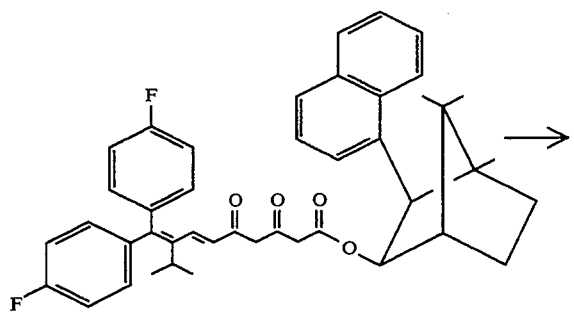

The β,δ-diketocarboxylic acid ester (67 mg, 0.1 mmol) obtained in Example 8 was dissolved in a solvent mixture of THF (1 ml) and methanol (0.25 ml). Diethylmethoxyborane (11 mg, 15 μl, 0.11 mmol) was then added at −78° C. under argon atmosphere. The mixture was stirred at room temperature for 10 minutes and then cooled again at −78° C. Sodium borohydride (19 mg, 0.5 mmol) was added thereto, and the whole was stirred at −78° C. for 3 hours. The mixture was warmed gradually to room temperature and stirred overnight. Then, acetic acid (2 ml) was added thereto, and the whole was stirred for 10 minutes to terminate the reaction, diluted with water (10 ml), and extracted with ethyl acetate (20 ml×twice). The organic layer was washed with 5M sodium hydrogen carbonate aq solution and saturated sodium chloride aq solution and then dried over anhydrous magnesium sulfate. The organic layer was concentrated in vacuo to give a crude product. Methanol was added to the product and was then removed under heating. This operation was repeated 6 times to decompose the boron chelates formed. The residue was purified by thin layer chromatography (silica gel, ethyl acetate:hexane=3:7) to give 56 mg (83% yield) of (4S)-4,7,7-trimethyl-3-exo-(1-naphthyl)bicyclo[2.2.1]heptan-2-exo-yl (3S, 5R, 6E)-3,5-dihydroxy-9-methyl-8-bis(4-fluorophenyl)methylidene-6-decenoate. R_f=0.39 (hexane:ethyl acetate=2:1) [α]_D^{20}=−93.32° (c 5.00, CHCl₃) IR (CHCl₃): 3575, 2960, 2875, 1725, 1600, 1500, 1465, 1400, 1175, 1090, 1010, 1000, 835 cm⁻¹.

¹H NMR (CDCl₃): δ=0.79-0.98 (m, 2H), 1.00 (s, 3H), 1.05 (d, J =5.8 Hz, 3H), 1.07 (d, J=5.8 Hz, 3H), 1.26 (s, 3H), 1.32 (s, 3H), 1.45-1.54 (m, 1H), 1.56 (br s, 1H, OH), 1.59-1.63 (m, 2H), 1.72-1.85 (m, 2H), 1.92-2.00 (m, 2H), 2.77-2.85 (m, 1H), 2.94-2.99 (m, 1H), 3.82-3.86 (m, 1H), 4.08 (d, J=8.8 Hz, 1H), 5.38 (dd, J=6.35, 16.2 Hz, 1H), 5.51 (d, J=8.8 Hz, 1H), 6.04 (dd, J=1.1, 16.2 Hz, 1H) 6.86 (m, 8H), 7.38-8.05 (m, 7H). MS:m/z (rel. intensity) 679 (M⁺, trace), 269 (13), 264 (22), 263 (100), 207 (44), 170 (22), 141 (39), 109 (20).

REFERENTIAL EXAMPLE 7

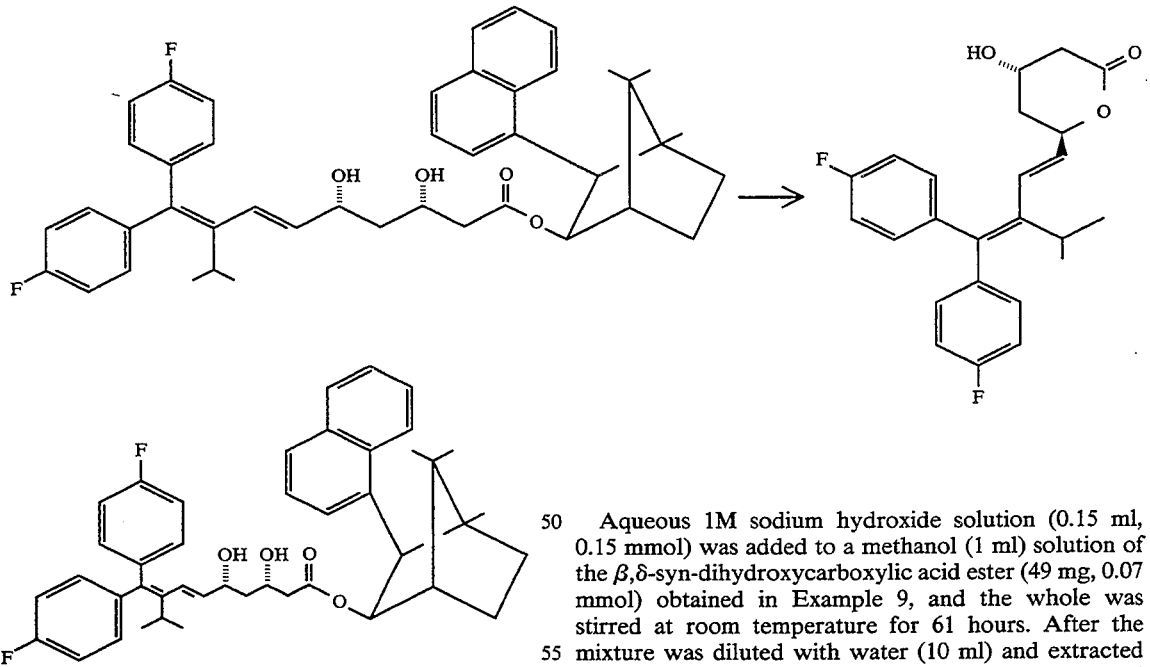

Aqueous 1M sodium hydroxide solution (0.15 ml, 0.15 mmol) was added to a methanol (1 ml) solution of the β,δ-syn-dihydroxycarboxylic acid ester (49 mg, 0.07 mmol) obtained in Example 9, and the whole was stirred at room temperature for 61 hours. After the mixture was diluted with water (10 ml) and extracted with diethyl ether (10 ml×twice) to remove neutral substances, the aqueous layer was neutralized with cold 1M hydrochloric acid (0.5 ml) and extracted with diethyl ether (10 ml×3 times). The ethereal layer was washed with saturated sodium chloride aq solution, dried over anhydrous magnesium sulfate, and concentrated in vacuo. The resulting crude carboxylic acid was dissolved in toluene (3 ml), and the solution was heated under reflux at 110° C. for 5 hours under argon atmosphere. After removing the toluene in vacuo, the residue was purified by thin layer chromatography to give 18 mg (63% yield) of (3S, 5R, 6E)-3,5-dihydroxy-9-methyl-8-bis(4-fluorophenyl)methylidene-6-decen- 1,5-olide. $R_f=0.63$ (dichloromethane:acetone=10:1) $[\alpha]_D^{20} -91.03°$ (C 0.36, CHCl$_3$)

HPLC analysis (CHIRAL AD column, hexane:isopropyl alcohol=40:1) of the product showed that a trans:cis ratio was 83:17, enantiomer excess of the trans-isomer being 66% ee. The trans-isomer was separated by liquid chromatography. IR (CHCl$_3$): 3650, 2940, 2875, 1735, 1605, 1505, 1405, 1365, 1260, 1235, 1160, 1130, 1095, 1060, 1040, 970, 835, 800 cm$^{-1}$.

$^1$H NMR (CDCl$_3$): $\delta=1.09$ (d, J=5.4 Hz, 3H), 1.11 (d, J=5.4 Hz, 3H), 1.46–1.65 (m, 1H), 1.75–1.81 (m, 1H), 2.54–2.61 (m, 1H), 2.70 (dd, J=5.0, 17.7 Hz, 1H), 2.82–2.91 (m, 1H), 4.22–4.26 (m, 1H), 5.01–5.06 (m, 1H), 5.55 (dd, J=6.8, 16.2 Hz, 1H), 6.23 (dd, J=1.2, 16.2 Hz, 1H), 6.91–7.09 (m, 8H).

EXAMPLE 10

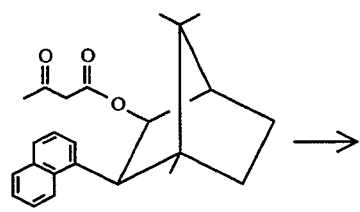

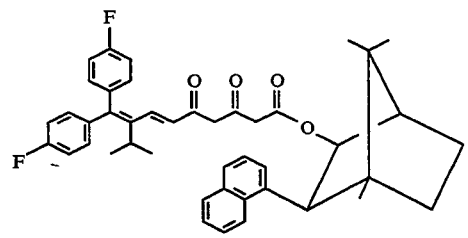

Sodium hydride (content 60%, oil dispersion, 41 mg, 1.01 mmol) was washed with hexane and suspended in THF (5 ml) under argon atmosphere. To the suspension was added a THF (2 ml) solution of the acetoacetate (0.36 g, 1.0 mmol) obtained in Referential Example 4. The mixture was stirred for 0.5 hours, cooled to −10° C., and treated with butyllithium (1.52M hexane solution, 0.65 ml, 1.0 mmol). The whole was stirred at −10° C. for 0.5 hours. The resulting dianion was treated with a THF (1 ml) solution of the N-methyl-N-methoxyamide (0.37 g, 1.0 mmol) obtained in Referential Example 6. After stirring at −10° C. for 2 hours and at room temperature overnight, the mixture was cooled to 0° C., treated with 1M hydrochloric acid (0.5 ml) to terminate the reaction, and diluted with ethyl acetate (25 ml). The organic layer was washed with water (20 ml×twice) and saturated sodium chloride aq solution and then dried over anhydrous magnesium sulfate. Removal of the solvent in vacuo afforded 0.64 g of a crude product which was purified by thin layer chromatography to give 0.26 g (38% yield) of (4R)-4,7,7-trimethyl-3-exo-(1-naphthyl)bicyclo[2.2.1]heptan-2-exo-yl (6E)-3,5-dioxo-9-methyl-8-bis(4-fluorophenyl)methylidene-6-decenoate and 0.18 g of the starting acetoacetate recovered. The yield of the desired product was calculated to be 75% based on the starting acetoacetate consumed. $R_f=0.28$ (hexane:dichloromethane=1:1) $[\alpha]_D^{20} = +112.45°$ (c 1.05, CHCl$_3$) IR (KBr): 3070, 2975, 2900, 1735, 1605, 1505, 1440, 1320, 1225, 1160, 1095, 1020, 840, 785 cm$^{-1}$.

$^1$H NMR (CDCl$_3$): $\delta=0.80$–2.13 (br m, 11H), 1.00 (s, 3H), 1.33 (s, 3H), 1.36 (s, 3H), 2.83–3.23 (m, 1H), 4.07 (d, 1H, J=9 Hz), 4.73 (s, 1H), 5.55 (d, J=19.5 Hz, 1H), 5.90 (d, J=16.5 Hz, 1H), 6.80–8.10 (m, 16H).

EXAMPLE 11

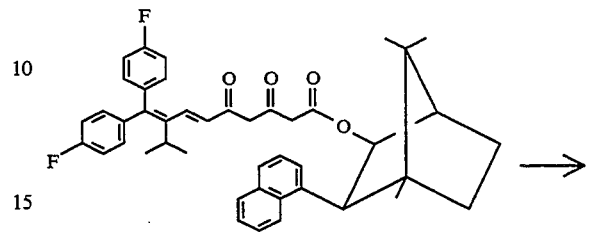

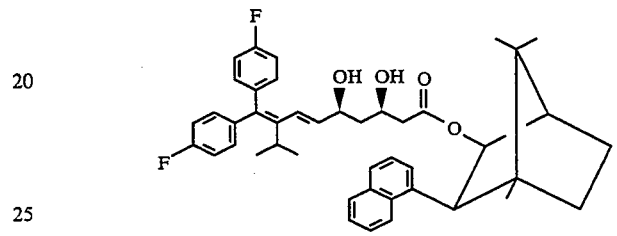

The $\beta,\delta$-diketocarboxylic acid ester (0.100 g, 0.15 mmol) obtained in Example 10 was dissolved in a solvent mixture of THF (1 ml) and methanol (0.2 ml). Diethylmethoxyborane (16 mg, 22 μl, 0.16 mmol) was added thereto at −78° C. under argon atmosphere. The mixture was stirred at room temperature for 10 minutes and then cooled again to −78° C. Sodium borohydride (19 mg, 0.5 mmol) as added thereto, and the whole was stirred at −78° C. for 3 hours and at room temperature overnight. Then, acetic acid (2 ml) was added thereto, and the mixture was stirred for 10 minutes, diluted with water (10 ml), and extracted with ethyl acetate (20 ml×twice). The organic layer was washed successively with 5M sodium hydrogen carbonate aq solution and saturated sodium chloride aq solution and then dried over anhydrous magnesium sulfate. After concentrating in vacuo, methanol was added to the residue and then removed under heating. This operation was repeated 5 times to decompose the boron chelates formed. The residue was purified by thin layer chromatography (silica gel, ethyl acetate:hexane=3:7) to give 76 mg (79% yield) of (4R)-4,7,7-trimethyl-3-exo-(1-naphthyl)-bicyclo[2.2.1]heptan-2-exo-yl (3R, 5S, 6E)-3,5-dihydroxy-9-methyl-8-bis(4-fluorophenyl)methylidene-6-decenoate. $R_f=0.38$ (hexane:ethyl acetate=2:1) $[\alpha]_D^{20}=+84.32°$ (c 1.25, CHCl$_3$) IR (CHCl$_3$): 3575, 2970, 2875, 1725, 1600, 1505, 1460, 1400, 1155, 1095, 1015, 1000, 835 cm$^{-1}$.

$^1$H NMR (CDCl$_3$): $\delta=0.79$–0.98 (m, 2H), 1.01 (s, 3H), 1.05 (d, J=5.8 Hz, 3H), 1.07 (d, J=5.8 Hz, 3H), 1.26 (s, 3H), 1.32 (s, 3H), 1.45–1.54 (m, 1H), 1.57–1.61 (m, 4H), 1.72–1.85 (m, 2H), 1.92–2.00 (m, 2H), 2.77–2.85 (m, 1H), 2.95–2.99 (m, 1H), 3.82–3.86 (m, 1H), 4.08 (d, J=8.8 Hz, 1H), 5.38 (dd, J=6.4, 16.2 Hz, 1H), 5.51 (d, J=8.8 Hz, 1H), 6.04 (dd, J=1.1, 16.2 Hz, 1H), 6.86 (m, 8H), 7.38–8.05 (m, 7H). MS:m/z (rel. intensity) 678 (M+, trace), 269 (14), 264 (22), 263 (100), 207 (52), 193 (12), 179 (15), 170 (35), 165 (12), 155 (14), 141 (57), 109 (27), 95 (14), 69 (15), 43 (41).

REFERENTIAL EXAMPLE 8

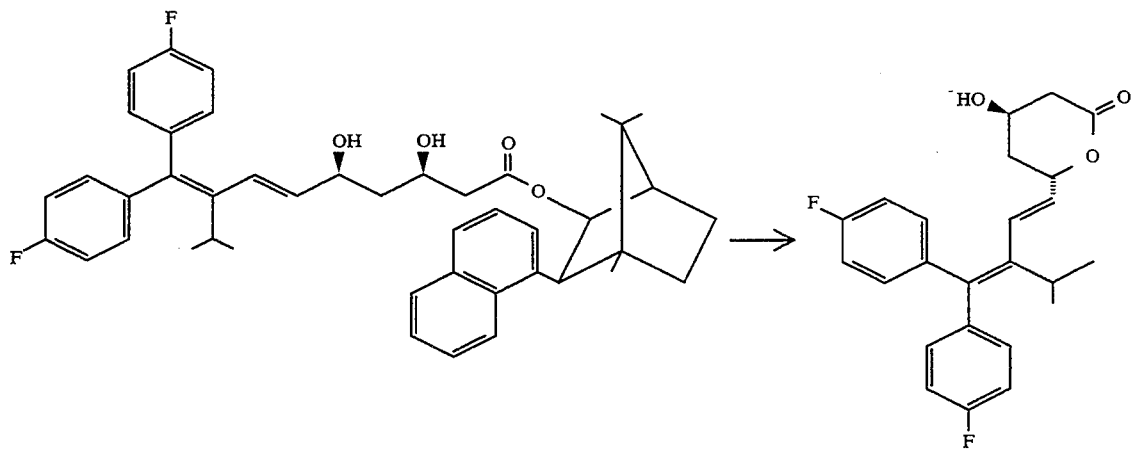

Aqueous 1M sodium hydroxide solution (0.16 ml, 0.16 mmol) was added to a methanol (2 ml) solution of the β,δ-syn-dihydroxycarboxylic acid ester (55 mg, 0.081 mmol) obtained in Example 11, and the whole was stirred at room temperature for 29 hours. The mixture was diluted with water (5 ml) and extracted with diethyl ether (5 ml×twice) to remove neutral substances. The aqueous layer was neutralized with 1M hydrochloric acid (1 ml) and extracted with diethyl ether (15 ml×3 times). The ethereal layer was washed with saturated sodium chloride aq solution, dried over anhydrous magnesium sulfate, and finally concentrated in vacuo. The resulting crude carboxylic acid was dissolved in toluene (3 ml), and the whole was heated at 110° C. for 5 hours under argon atmosphere. Concentration in vacuo followed by purification by thin layer chromatography (silica gel, ethyl acetate:hexane=3:7) gave 21 mg (65% yield) of (3R, 5S, 6E)-3,5-dihydroxy-9-methyl-8-bis(4-fluorophenyl)methylidene-6-decen-1,5-olide. This product was found to be a mixture of trans-isomer and cis-isomer in a ratio of 79:21. Purification by thin layer chromatography (dichloromethane:acetone=4:1) afforded the pure trans-isomer. HPLC analysis of the product showed an optical purity of 64% ee. $R_f$=0.36 (dichloromethane:acetone=10:1) $[\alpha]_D^{20}$=+113.4° (c 0.67, CHCl$_3$) IR (CHCl$_3$): 3625, 2950, 2925, 1725, 1600, 1500, 1400, 1360, 1230, 1155, 1090, 1060, 1035, 970, 835 cm$^{-1}$.

$^1$H NMR (CDCl$_3$): δ=1.09 (d, J=5.4 Hz, 3H), 1.11 (d, J=5.4 Hz, 3H), 1.46–1.65 (m, 1H), 1.75–1.81 (m, 1H), 2.54–2.61 (m, 1H), 2.70 (dd, J=5.0, 1.77 Hz, 1H), 2.82–2.91 (m, 1H), 4.22–4.26 (m, 1H), 5.01–5.06 (m, 1H), 5.55 (dd, J=6.8, 16.2 Hz, 1H), 6.23 (dd, J=1.2, 16.2 Hz, 1H), 6.91–7.09 (m, 8H).

EXAMPLE 12

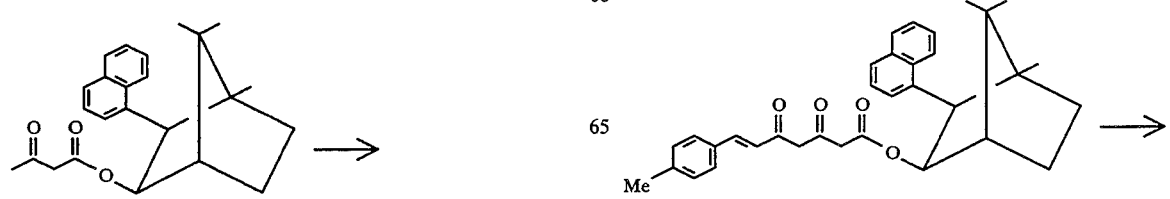

Following a procedure analogous to Example 1, a THF (5 ml) solution of the acetoacetate (1.09 g, 3.0 mmol) obtained in Referential Example 2 was allowed to react with a THF (15 ml) suspension of sodium hydride (132 mg, content 60%, oil dispersion, 3.3 mmol) and a hexane solution of butyllithium (1.55M, 2.0 ml, 3.1 mmol) successively. The resulting dianion was then treated with N-methoxy-N-methyl-(E)-3-(4-methylphenyl)propenamide (0.62 g, 3.0 mmol) to give 0.49 g (32% yield) of (4S)-4,7,7-trimethyl-3-exo-(1-naphthyl)-bicyclo[2.2.1]heptan-2-exo-yl (E)-7-(4-methylphenyl)-3,5-dioxo-6-heptenoate together with 0.53 g of the starting acetoacetate recovered. The yield of the desired product was calculated to be 62% based on the starting material consumed. $R_f$=0.17 (hexane:dichloromethane=1:1) $[\alpha]_D^{20}$=−145.36° (c 0.63, CHCl$_3$) IR (CHCl$_3$): 2925, 2850, 1720, 1625, 1570, 1500, 1475, 1425, 1325, 1245, 1150, 1115, 1075, 1005, 960, 800 cm$^{-1}$.

$^1$H NMR (CDCl$_3$): δ=0.80–2.1 (br m, 5H), 1.00 (s, 3H), 1.22 (s, 3H), 1.30 (s, 3H), 2.40 (s, 3H), 2.63 (s, 2H), 4.08 (d, J=9 Hz, 1H), 4.80 (s, 1H), 5.58 (d, J=9 Hz, 1H), 6.22 (d, J=15 Hz, 1H), 7.13–8.13 (m, 12H). MS:m/z (rel. intensity) 508 (M$^+$, 7), 398 (2), 280 (4), 262 (11), 229 (44), 187 (62), 170 (100), 169 (13), 165 (12), 145 (45), 142 (13), 141 (27), 115 (15), 41 (13).

EXAMPLE 13

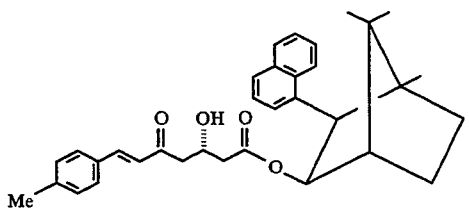

A toluene solution of diisobutylaluminium hydride (1.02M solution, 0.70 ml, 0.72 mmol) was added at −78° C. to a THF (1.5 ml) solution of the β,δ-diketocarboxylic acid ester (0.173 g, 0.34 mmol) obtained in Example 12 and the whole was stirred for 4 hours. After workup of the mixture similar to Example 3, the resulting crude product was purified by thin layer chromatography (silica gel, ethyl acetate:hexane=1:4) to give 0.135 g (78% yield) of (4S)-4,7,7-trimethyl-3-exo-(1-naphthyl)-bicyclo[2.2.1]heptan-2-exo-yl (3S, 6E)-3-hydroxy-5-oxo-7-(4-methylphenyl)-6-heptenoate. $R_f$=0.36 (hexane:ethyl acetate=3:1) $[\alpha]_D^{20}$=−108.90° (c 1.50, CHCl$_3$)

HPLC analysis (silica gel 60, hexane:ethanol=80:1) of the product showed that its diastereomer ratio was 95.5:4.5. The isomer shown in the above scheme was obtained as main product. IR (CHCl$_3$): 3560, 2940, 2860, 1720, 1670, 1640, 1595, 1560, 1500, 1480, 1455, 1435, 1385, 1320, 1255, 1175, 1080, 1010, 970, 790 cm$^{-1}$.

$^1$H NMR (CDCl$_3$): δ=1.80-2.23 (m, 10H), 1.00 (s, 3H), 1.23 (s, 3H), 1.33 (s, 3H), 2.40 (s, 3H), 3.40-3.76 (m, 1H), 4.10 (d, J=9 Hz, 1H), 5.57 (d, J=9 Hz, 1H), 6.50 (d, J=15.75 Hz, 1H), 7.16-8.13 (m, 12H). MS:m/z (rel. intensity) 510 (M$^+$, 1), 492 (1), 262 (14), 240 (26), 231 (19), 213 (22), 179 (10), 171 (13), 170 (100), 169 (11), 165 (15), 145 (92), 141 (29), 117 (17), 115 (20), 91 (13), 71 (13), 43 (21).

EXAMPLE 14

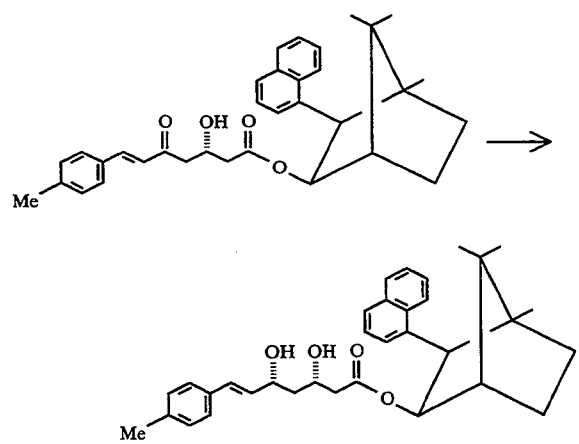

The β-hydroxy-δ-ketocarboxylic acid ester (49 mg, 0.10 mmol) obtained in Example 13 in a solvent mixture of THF (1 ml) and methanol (0.2 ml) was allowed to react with diethylmethoxyborane (13 μl, 9.6 mg, 0.10 mmol) and sodium borohydride (8 mg, 0.21 mmol), successively, as described in Example 4. Workup and purification by thin layer chromatography (silica gel, ethyl acetate:hexane=3:7) afforded 40 mg (81% yield) of (4S)-4,7,7-trimethyl-3-exo-(1-naphthyl)bicyclo[2.2.1-]heptan-2-exo-yl (3S, 5R, 6E)-3,5-dihydroxy-7-(4-methylphenyl)-6-heptenoate. $R_f$=0.31 (hexane:ethyl acetate=2:1) $[\alpha]_D^{20}$=−87.0° (c 3.00, CHCl$_3$)

HPLC analysis (silica gel 60, hexane:ethanol=40:1) of the product confirmed that it was composed of a single diastereomer. IR (CHCl$_3$): 3550, 3460, 2940, 2860, 1720, 1595, 1505, 1480, 1390, 1250, 1175, 1150, 1080, 1010, 960, 845, 790, 780 cm$^{-1}$.

$^1$H NMR (CDCl$_3$): δ=1.01 (s, 3H), 1.08-1.22 (m, 2H), 1.27 (s, 3H), 1.33 (s, 3H), 1.45-1.53 (m, 1H), 1.57-1.68 (m, 3H), 1.73-1.84 (m, 2H), 1.88-2.01 (m, 3H), 2.33 (s, 3H), 3.07-3.13 (m, 1H), 4.09 (d, J=8.8 Hz, 1H), 4.12-4.16 (m, 1H), 5.53 (d, J=8.8 Hz, 1H), 5.95 (dd, J=6.3, 15.9 Hz, 1H), 6.47 (d, J=15.9 Hz, 1H), 7.12 (d, J=8.0 Hz, 2H), 7.24 (d, J=8.0 Hz, 2H), 7.41-7.53 (m, 3H), 7.65 (d, J=7.4 Hz, 1H) 7.73 (d, J=8.2 Hz, 1H), 7.87 (dd, J=1.2, 8.0 Hz, 1H), 8.05 (d, J=8.5 Hz, 1H). MS:m/z (rel. intensity) 512 (M$^+$, 1), 264 (16), 263 (68), 262 (16), 249 (31), 231 (23), 215 (17), 207 (41), 197 (16), 193 (13), 181 (14), 179 (22), 173 (14), 171 (16), 170 (100), 169 (28), 167 (14), 165 (23), 155 (35), 145 (43), 142 (16), 141 (73), 131 (24), 129 (35), 128 (15), 124 (14), 109 (23), 105 (37), 95 (20), 91 (17), 71 (20), 69 (17), 55 (17): 43 (22), 41 (32).

REFERENTIAL EXAMPLE 9

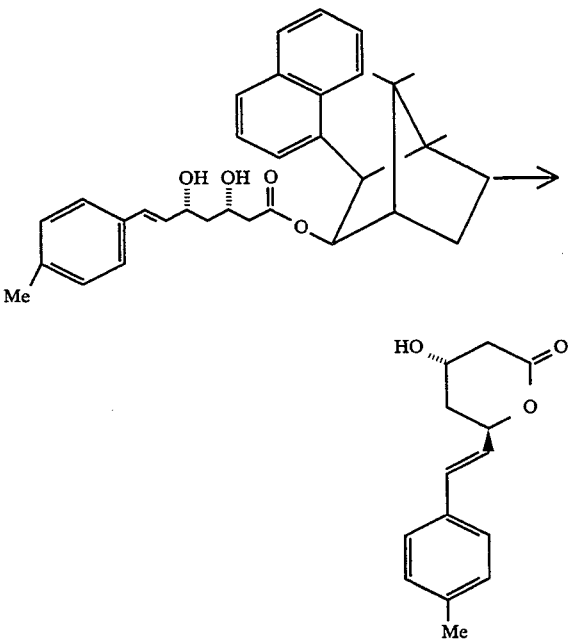

Following a procedure analogous to Referential Example 3, the β,δ-syn-dihydroxycarboxylic acid ester (30 mg, 0.06 mmol) obtained in Example 14 was hydrolyzed with methanol (2 ml)-1M sodium hydroxide aq solution (0.15 ml) at room temperature over a period of 45 hours. After workup as before, the resulting carboxylic acid was dissolved in toluene (3 ml), and the whole was heated at 110° C. for 5 hours to lactonize the acid. Purification by thin layer chromatography afforded 8.2 mg (60% yield) of (3S, 5R, 6E)-3,5-dihydroxy-7-(4-methylphenyl)-6-hepten-1,5-olide. HPLC analysis (CHIRAL OA and CHIRAL AD column) of the product showed an optical purity of 92% ee. $R_f$=0.32 (dichloromethane:acetone=10:1) $[\alpha]_D^{20}$=−5.69° (c 0.65, CHCl$_3$) mp=126°-127° C. IR (KBr): 3400, 2925, 2850, 1695, 1515, 1380, 1315, 1245, 1165, 1065, 1035, 975, 875, 800 cm$^{-1}$.

$^1$H NMR (CDCl$_3$): δ=1.93–2.00 (m, 1H), 2.08–2.15 (m, 1H), 2.34 (s, 3H), 2.64–2.70 (m, 1H), 2.80 (dd, J=5.0, 17.7 Hz, 1H), 4.42–4.46 (m, 1H), 5.33–5.38 (m, 1H), 6.15 (dd, J=6.5, 15.9 Hz, 1H), 6.67 (d, J=15.9 Hz, 1H), 7.13 (d, J=8.0 Hz, 2H), 7.28 (d, J=8.0 Hz, 2H). MS:m/z (rel. intensity) 232 (M$^+$, 19), 214 (6), 145 (17), 144 (14), 131 (18), 129 (40), 128 (20), 119 (17), 118 (100), 117 (19), 115 (17), 105 (43), 91 (21), 44 (22), 43 (38).

EXAMPLE 15

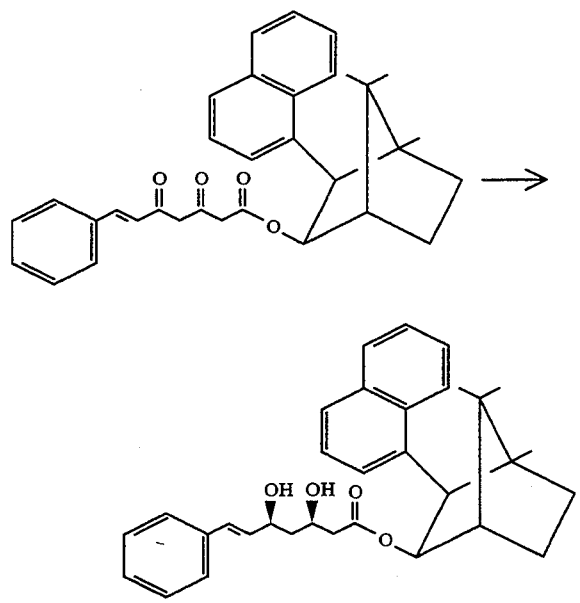

The optically active diketocarboxylic acid ester (100 mg, 0.20 mmol) obtained in Example 1 was dissolved in a solvent mixture of THF (2.0 ml) and methanol (0.5 ml). Then, dimethylbromoborane (25 μl, 0.22 mmol) was added thereto at −78° C. under argon atmosphere. The mixture was stirred at room temperature for 15 minutes and then cooled again to −78° C. Thereto was added sodium borohydride (38 mg, 1.0 mmol). After stirring at −78° C. for 4 hours, the mixture was gradually warmed to room temperature and stirred for 8 hours. Then, acetic acid (0.5 ml) was added to terminate the reaction, and the mixture was diluted with diethyl ether, washed with 5% sodium hydrogen carbonate aq solution (ca. 20 ml), and then dried over anhydrous magnesium sulfate. The organic layer was concentrated in vacuo to give a crude product. Methanol (10 ml) was added to the product and then removed in vacuo. This operation was repeated 10 times to decompose and evaporate organoboron compounds. The resulting crude product was purified by column chromatography (silica gel, hexane:ethyl acetate=4:1) to give 95 mg (95% yield) of (4S)-4,7,7-trimethyl-3-exo-(1-naphthyl)-bicyclo[2.2.1]heptan-2-exo-yl (3R, 5S, 6E)-7-phenyl-3,5-dihydroxy-6-heptenoate. R$_f$=0.27 (hexane:ethyl acetate=2:1) IR (CHCl$_3$): 3550, 2950, 1730, 1600, 1400, 1210, 1095 cm$^{-1}$.

$^1$H NMR (CDCl$_3$): δ=1.01 (s, 3H), 1.26 (s, 3H), 1.33 (s, 3H), 1.03–1.98 (br m, 11H), 2.26–2.57 (m, 1H), 3.05–3.45 (m, 1H), 4.07–4.27 (m, 2H), 5.56 (d, J=9.0 Hz, 1H), 6.01 (dd, J=6.0, 16 Hz, 1H), 6.50 (d, J=16 Hz, 1H), 7.21–7.53 (m, 8H), 7.64 (d, J=7.0 Hz, 1H), 7.73 (d, J=8.0 Hz, 1H), 7.83 (d, J=8.0 Hz, 1H), 8.04 (d, J=8.0 Hz, 1H). MS:m/z (rel. intensity) 498 (M$^+$, 3), 480 (M$^+$-H$_2$O), 463 (M$^+$-2H$_2$O, 5), 263 (79), 170 (100), 141 (84). [α]$_D^{20}$=−109.1° (c 1.03, CHCl$_3$)

EXAMPLE 16

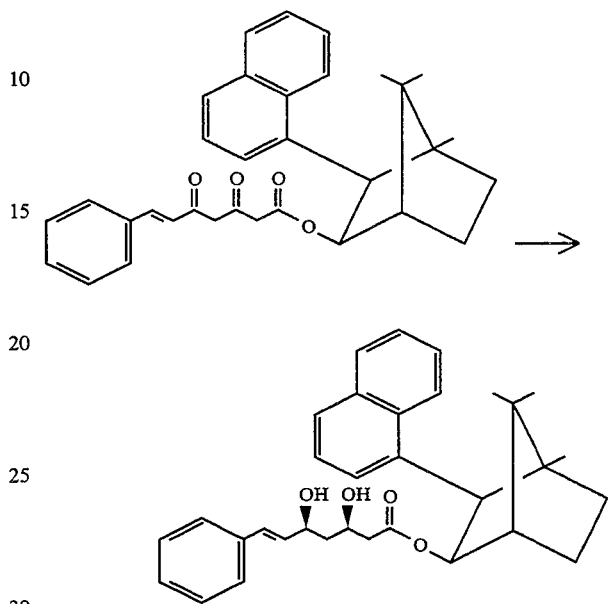

The same product (90 mg, 90% yield) of Example 15 was obtained according to the procedure of Example 15 when dimethylethoxyborane (34 μl, 0.22 mmol) was used instead of dimethylbromoborane. [α]$_D^{20}$=−109.1° (c 1.01, CHCl$_3$)

Other spectral data of the product were identical with those of the product obtained in Example 15.

REFERENTIAL EXAMPLE 10

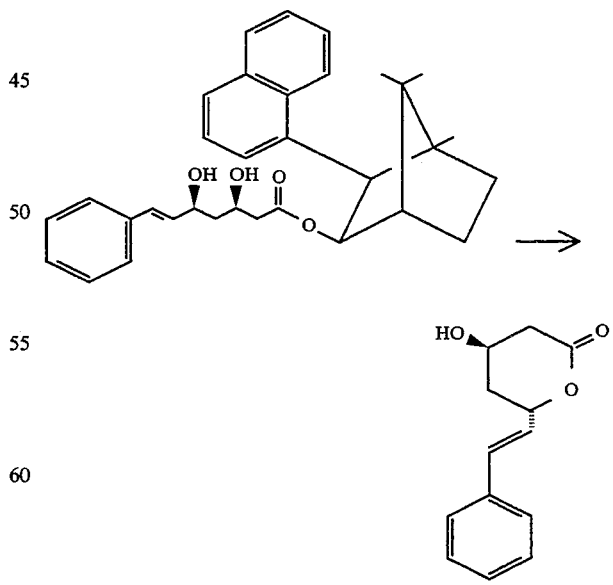

Following the procedure described in Referential Example 3, the β,δ-syn-dihydroxycarboxylic acid ester (80 mg, 0.16 mmol) obtained in Example 15 was converted into (3R,5S,6E)-3,5 dihydroxy-7-phenyl-6-hepten-1,5-olide (15 mg, 43% yield). HPLC analysis (CHIRAL OA column, hexane:isopropyl alcohol=9:1) of the product showed that a cis:trans ratio of 24:76 and an optical purity of 42% ee. [α]$_D^{20}$= +2.66° (c 0.30, CHCl$_3$)

The other spectral data of the product were identical with those of the product obtained in Referential Example 3.

REFERENTIAL EXAMPLE 11

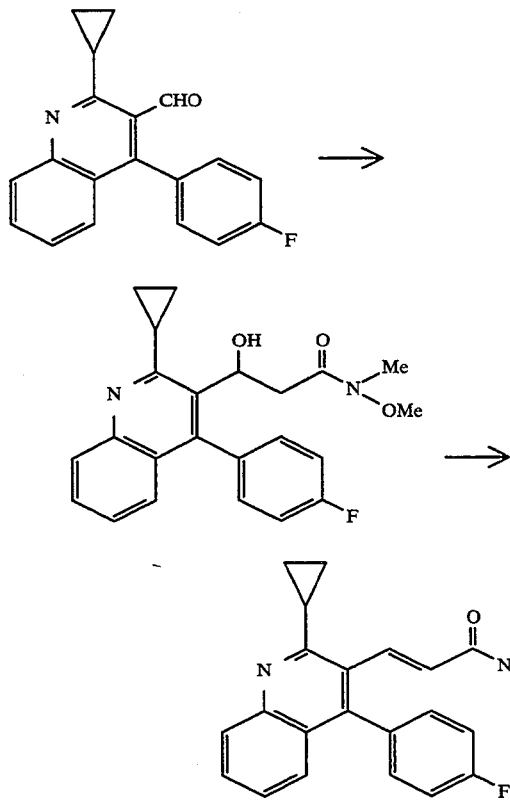

Butyllithium (1.64M hexane solution, 7.54 ml, 12.4 mmol) was added to a THF (40 ml) solution of diisopropylamine (1.25 g, 12.4 mmol) at −78° C. and the mixture was stirred for 15 minutes. Thereto was added a THF (20 ml) solution of N-methoxy-N-methylacetamide (1.27 g, 12.3 mmol) at −78° C., and the resulting mixture was stirred at −78° C. for 15 minutes. To this mixture was added a THF (40 ml) solution of 2-cyclopropyl-4-(4-fluorophenyl)-3-formylquinoline (3.00 g, 10.3 mmol). The reaction mixture was stirred at −78° C. to room temperature over a period of 3 hours before quenching with water and extraction with diethyl ether. The ethereal organic layer was washed with saturated sodium chloride aq solution, dried over magnesium sulfate, and concentrated in vacuo. The residue was purified by column chromatography (hexane:ethyl acetate=2:1) to give N-methoxy-N-methyl-3-{2-cyclopropyl-4-(4-fluorophenyl)quinoline-3-yl}-3-hydroxypropanamide (3.70 g, 91% yield). R$_f$=0.30 (hexane:ethyl acetate=2:1) IR (CHCl$_3$): 3450, 3000, 1640, 1515, 1490, 1420, 1230, 1070, 780 cm$^{-1}$.

$^1$H NMR (CDCl$_3$): δ=1.02–1.16 (m, 3H), 1.74–1.79 (m, 1H), 2.66 (d, J=17.2 Hz, 1H), 3.17 (s, 3H), 3.16–3.24 (m, 1H), 3.52 (dd, J=17.2, 11.3 Hz, 1H), 3.62 (s, 3H), 4.14 (d, J=2.4 Hz, 1H), 5.35 (dt, J=11.3, 2.4 Hz, 1H), 7.12–7.35 (m, 6H), 7.58 (dd, J=6.8, 1.4 Hz, 1H), 7.92 (dq, J=8.4, 0.6 Hz, 1H). MS:m/z (rel. intensity) 394 (M+, 11), 363, (M+,-OMe, 46), 334 (58), 292 (100), 274 (38), 263 (37).

A dichloromethane (10 ml) solution of methanesulfonyl chloride (1.44 g, 12.6 mmol) was added to a dichloromethane (40 ml) solution of N-methoxy-N-methyl-3-{2-cyclopropyl-4-(4-fluorophenyl)quinolin-3-yl}-3-hydroxypropanamide (3.30 g, 8.38 mmol) and triethylamine (1.27 g, 12.6 mmol). The resulting mixture was stirred at 0° C. for 30 minutes and at room temperature for 3 hours before treatment with triethylamine (1.27 g, 12.6 mmol). The mixture was heated to reflux for 3 hours, quenched with saturated NaHCO$_3$ aq solution, and extracted with dichloromethane. The organic layer was washed with saturated NaCl aq solution, dried over magnesium sulfate, and then concentrated. The residue was purified by column chromatography (hexane:ethyl acetate=3:1) to give N-methoxy-N-methyl-(E)-3-{2-cyclopropyl-4-(4-fluorophenyl)quinolin-3-yl}propenamide (2.52 g, 80% yield). mp=141° C. R$_f$=0.52 (hexane:ethyl acetate=2:1) IR (CHCl$_3$): 3000, 1650, 1610, 1515, 1490, 1415, 1385, 1220, 1090, 1025, 840, 760 cm$^{-1}$.

$^1$H NMR (CDCl$_3$): δ=1.05–1.09 (m, 2H), 1.37–1.40 (m, 2H), 2.40 (m, 1H), 3.21 (s, 3H), 3.49 (s, 3H), 6.46 (d, J=16.1 Hz, 1H), 7.16–7.27 (m, 4H), 7.30–7.37 (m, 2H), 7.62 (dd, J=6.2, 2.0 Hz, 1H), 7.89 (d, J=16.1 Hz, 1H), 7.96 (d, J=8.2 Hz, 1H). MS: m/z (rel. intensity) 376 (M+, 9), 316 (48), 288 (51), 260 (12), 185 (14), 129 (11), 43 (100).

EXAMPLE 17

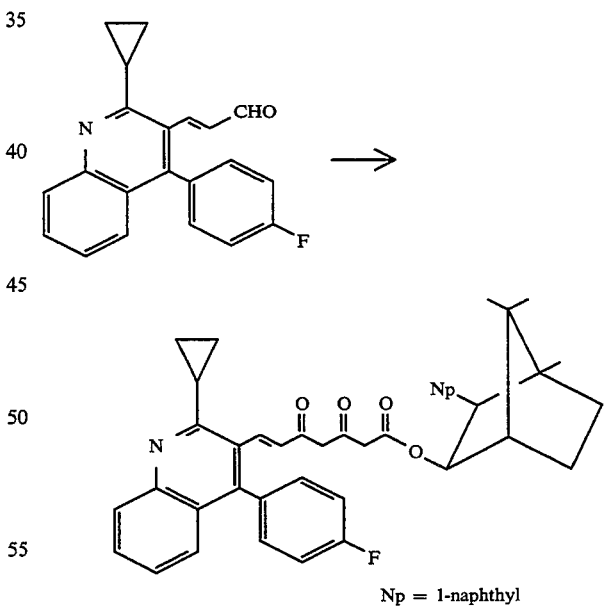

Np = 1-naphthyl

To a THF (20 ml) suspension of sodium hydride (60% in oil, 0.26 g, 6.50 mmol) was added a THF (30 ml) solution of (4 S )-4,7,7-trimethyl-3-exo-(1-naphthyl)-bicyclo[2.2.1]heptan2-exo-yl acetoacetate (2.37 g, 6.50 mmol) at 0° C., and the mixture was stirred for 15 min. To this mixture was added butyllithium (1.64 M hexane solution, 4.00 ml, 6.55 mmol) at 0° C., and the resulting mixture was cooled to −78° C. Thereto was added a THF (50 ml) solution of N-methoxy-N-methyl-(E)-3-{2-cyclopropyl-4-(4-fluorophenyl)quinolin-3- yl}propenamide (2.45 g, 6.51 mmol) as obtained in Example 16. The mixture was stirred at −78° C. to 0° C. over 3 hours before hydrolysis with 1M hydrochloric acid (20 ml), neutralization with saturated sodium hydrogen carbonate aq solution and extraction with ether. The organic layer was washed with saturated sodium chloride aq solution, dried over magnesium sulfate, and concentrated in vacuo. The residue was purified by column chromatography (hexane:ethyl acetate=15:1) to give (4S)-4,7,7-trimethyl-3-exo-(1-naphthyl)bicyclo[2.2.1]heptan-2-exo-yl (E)-7-{2-cyclopropyl-4-(4-fluorophenyl)quinolin-3-yl}-3,5-dioxo-6-heptenoate (2.12 g, 48% yield). Meantime the starting materials (4S)-4,7,7-trimethyl-3-exo-(1-naphthyl)bicyclo[2.2.1]heptan-2-exo-yl acetoacetate (0.60 g, 25%) and N-methoxy-N-methyl-(E)-3-{2-cyclopropyl-4-(4-fluorophenyl)quinolin-3-yl}propenamide (1.22 g, 50%) were recovered. $R_f$=0.48 (hexane:ethyl acetate=5:1) $[\alpha]_D^{20}$=−106.60° (c 1.03, CHCl$_3$) IR (CHCl$_3$): 2960, 1730, 1605, 1515, 1490, 1395, 1235, 1090, 1030 cm$^{-1}$.

$^1$H NMR (CDCl$_3$): δ=1.00 (s, 3H), 1.12 (dd, J=8.9, 3.0 Hz, 2H), 1.22 (s, 3H), 1.24 (s, 3H), 1.42–1.60 (m, 4H), 1.72–1.79 (m, 1H), 1.91–1.99 (m, 2H), 2.41 (m, 1H), 2.52 (d, J=14.8 Hz, 1H), 2.57 (d, J=14.8 Hz, 1H), 4.05 (d, J=8.7 Hz, 1H), 4.69 (s, 1H), 5.87 (d, J=16.2 Hz, 1H), 7.20–7.47 (m, 10H), 7.56 (m, 3H), 7.72 (dd, J=8.0, 1.1 Hz, 1H), 7.98 (d, J=8.4 Hz, 1H), 8.00 (d, J=8.4 Hz, 1H). MS: m/z (rel. intensity) 679 (M+, 0.5), 401 (3), 399 (32), 356 (8), 288 (50), 274 (22), 170 (100).

EXAMPLE 18

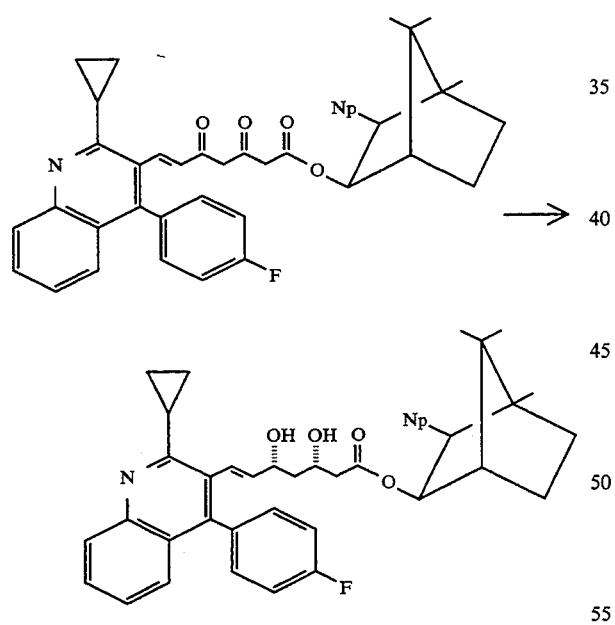

The diketocarboxylic acid ester (200 mg, 0.29 mmol) obtained in Example 17 was dissolved into a solvent mixture of THF (2.0 ml) and methanol (0.5 ml). Then, diethylmethoxyborane (32 mg, 0.32 mmol) was added thereto at −78° C. under argon atmosphere. The mixture was once warmed to room temperature under stirring over 15 minutes and then cooled again to −78° C. Thereto was added sodium borohydride (56 mg, 1.48 mmol). After stirring at −78° C. for 4 hours and at −78° C. to room temperature over 8 hours, the mixture was treated with acetic acid (0.5 ml) to terminate the reaction, poured into saturated sodium hydrogen carbonate aq solution and then extracted with diethyl ether. The organic layer was washed with saturated sodium chloride aq solution, dried over magnesium sulfate, and concentrated in vacuo. Methanol (10 ml) was added to dissolve the residue and then removed in vacuo. This operation was repeated 10 times to decompose and evaporate organoboron compounds. The resulting crude product was purified by column chromatography (hexane:ethyl acetate=15:1) to give (4S)-4,7,7-trimethyl-3-exo-(1-naphthyl)bicyclo[2.2.1]heptan-2-exo-yl (3S,5R,6E)-7-{2-cyclopropyl-4-(4-fluorophenyl)quinolin-3-yl}-3,5-dihydroxy-6-heptenoate (181 mg, 90% yield). $R_f$=0.36 (hexane:AcOEt=2:1) $[\alpha]_D^{20}$=−72.19° (c 1.00, CHCl$_3$) IR (CHCl$_3$): 3460, 3010, 2960, 1725, 1605, 1515, 1490, 1400, 1220, 1090, 790 cm$^{-1}$.

$^1$H NMR (CDCl$_3$): δ=0.80 (d, J=14.3 Hz, 1H), 0.88–0.96 (m, 1H), 1.02 (s, 3H), 1.00–1.05 (m, 2H), 1.27 (s, 3H), 1.33 (s, 3H), 1.31–1.37 (m, 2H), 1.46–1.55 (m, 1H), 1.57–1.63 (m, 2H), 1.75–1.82 (m, 1H), 1.83 (dd, J=15.4, 9.4 Hz, 1H), 1.92–1.98 (m, 1H), 2.00 (d, J=4.8 Hz, 1H), 2.39 (m, 1H), 2.92–2.99 (m, 1H), 3.03 (d, J=1.4 Hz, 1H), 3.95–3.99 (m, 1H), 4.08 (d, J=8.5 Hz, 1H), 5.40 (dd, J=16.2, 5.8 Hz, 1H), 5.52 (d, J=8.5 Hz, 1H), 6.50 (dd, J=16.2, 1.4 Hz, 1H), 7.07–7.18 (m, 4H), 7.27–7.34 (m, 2H), 7.38–7.44 (m, 2H), 7.50 (dd, J=7.0, 1.5 Hz, 1H), 7.58 (dd, J=6.3, 2.0 Hz, 1H), 7.65 (d, J=7.3 Hz, 1H), 7.69 (d, J=8.2 Hz, 1H), 7.80 (dd, J=8.0, 1.2 Hz, 1H), 7.94 (d, J=7.7 Hz, 1H), 8.04 (d, J=8.5 Hz, 1H). MS: m/z (rel. intensity) 683 (M+, 2), 644 (1), 420 (14), 288 (53), 275 (34), 170 (100).

REFERENTIAL EXAMPLE 12

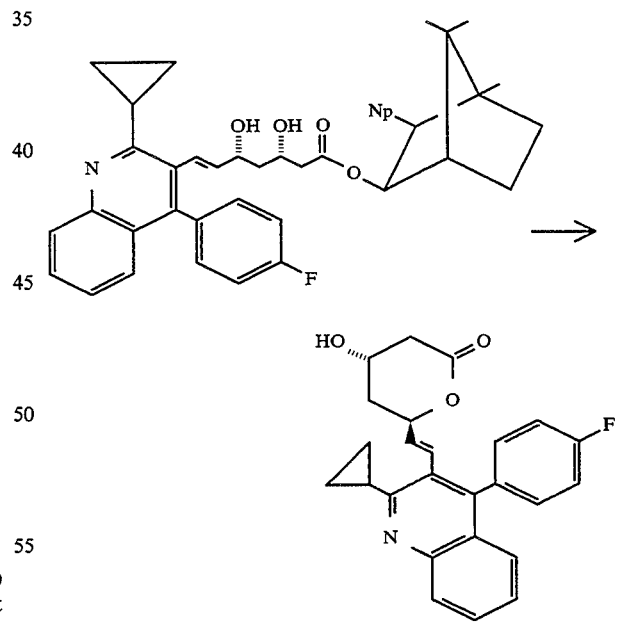

Aqueous 1M sodium hydroxide solution (0.5 ml) was added to a methanol (5.0 ml) solution of the dihydroxyester (70 mg, 0.10 mmol) obtained in Example 18. The mixture was stirred at room temperature for 12 hours. Then, the resulting mixture was poured into sodium acetate-acetic acid buffer (15 ml, pH=4–5) and extracted with ethyl acetate. The organic layer was washed with saturated sodium chloride aq solution, dried over anhydrous magnesium sulfate, and concentrated in vacuo. The residue was subjected to preparative thin layer chromatography (hexane:ethyl acetate=1:1) to separate the desired product from (4S)-4,7,7-trimethyl-3-exo-(1-naphthyl)bicyclo[2.2.1]heptan-2-exo-ol (26 mg, 91%). The desired product was then dissolved in toluene (25 ml), and the solution was heated under reflux for 12 hours. After removing the toluene in vacuo, the residue was purified by preparative thin layer chromatography (hexane:ethyl acetate=1:2) to give (3S,5R,6E)-7-{2-cyclopropyl-4-(4-fluorophenyl)quinolin-3-yl}-3,5-dihydroxy-6-hepten-1,5-olide (22 mg, 53% yield) as colorless foam. HPLC analysis (CHIRALPACK AS, hexane:isopropyl alcohol=9:1) of the product showed a cis:trans ratio of 77:23 and an optical purity of 58% ee. $R_f$=0.19 (hexane:AcOEt=2:1) $[\alpha]_D^{20}$= +14.77° (c 1.57, CHCl$_3$) IR (CHCl$_3$): 3440, 3005, 1730, 1600, 1560, 1510, 1490, 1410, 1230, 1155, 1060, 970, 830, 730 cm$^{-1}$.

$^1$H NMR (CDCl$_3$): δ=1.03–1.08 (m, 2H), 1.30–1.40 (m, 2H), 1.56–1.60 (m, 1H), 1.78 (m, 1H), 2.38 (m, 1H), 2.60 (ddd, J=7.4, 4.0, 1.5 Hz, 1H), 2.70 (dd, J=13.0, 4.8 Hz, 1H), 4.25 (m, 1H), 5.18 and 4.66 (m, 1H, ratio 77:23), 5.62 (dd, J=16.1, 6.2 Hz, 1H), 6.72 (dd, J=16.1, 1.4 Hz, 1H), 7.17–7.25 (m, 4H), 7.30–7.37 (m, 2H), 7.61 (dd, J=6.1, 2.1 Hz, 1H), 7.96 (d, J=8.3 Hz, 1H). MS: m/z (rel. intensity) 403 (M+, 9), 316 (11), 288 (100), 274 (12).

EXAMPLE 19

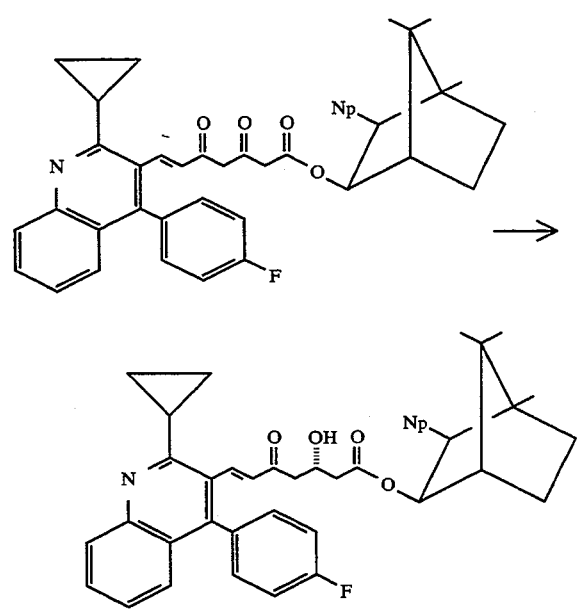

The diketocarboxylic acid ester (200 mg, 0.29 mmol) obtained in Example 17 was dissolved in THF (5.0 ml). Diisobutylaluminium hydride (0.70 ml, 1.00M in hexane, 0.70 mmol) was added thereto at −90° C. under argon atmosphere, and the whole was stirred at −90° C. for 24 hours. To the mixture was added saturated Na$_2$SO$_4$ aq solution (0.1 ml) to terminate the reaction. The resulting mixture was diluted with ethyl acetate (20 ml), dried over anhydrous magnesium sulfate and then concentrated in vacuo. The crude product was purified by column chromatography (hexane:ethyl acetate=4:1) to give (4S)-4,7,7-trimethyl-3-exo-(1-naphthyl)bicyclo[2.2.1]heptan-2-exo-yl (3S,6E)-7-{2-cyclopropyl-4-(4-fluorophenyl)quinolin-3-yl}-3-hydroxy-5-oxo-6-heptenoate (111 mg, 56% yield). $R_f$=0.13 (hexane:AcOEt=5:1) $[\alpha]_D^{20}$= −77.75° (C 0.98, CHCl$_3$) IR (CHCl$_3$): 2950, 1720, 1600, 1550, 1510, 1490, 1390, 1230, 1210, 1090, 1030 cm$^{-1}$.

$^1$H NMR (CDCl$_3$): δ=1.01 (s, 3H), 1.06 (m, 2H), 1.24 (s, 3H), 1.33 (s, 3H), 1.39–1.42 (m, 2H), 1.48–1.62 (m, 2H), 1.72–2.04 (m, 7H), 2.30 (m, 1H), 3.47–3.55 (m, 1H), 4.08 (d, J=8.7 Hz, 1H), 5.53 (d, J=8.7 Hz, 1H), 6.15 (d, J=16.5 Hz, 1H), 7.17–7.21 (m, 4H), 7.32–7.47 (m, 5H), 7.48 (d, J=16.5 Hz, 1H), 7.63–7.77 (m, 3H), 7.77 (dd, J=8.0, 1.2 Hz, 1H), 7.97 (d, J=8.4 Hz, 1H), 8.03 (d, J=8.4 Hz, 1H). MS: m/z (rel. intensity) 681 (M+, 0.6), 663 (M+-H$_2$O, 1), 402 (15), 384 (12), 350 (8), 331 (11), 316 (13), 288 (79), 240 (31), 170 (100).

EXAMPLE 20

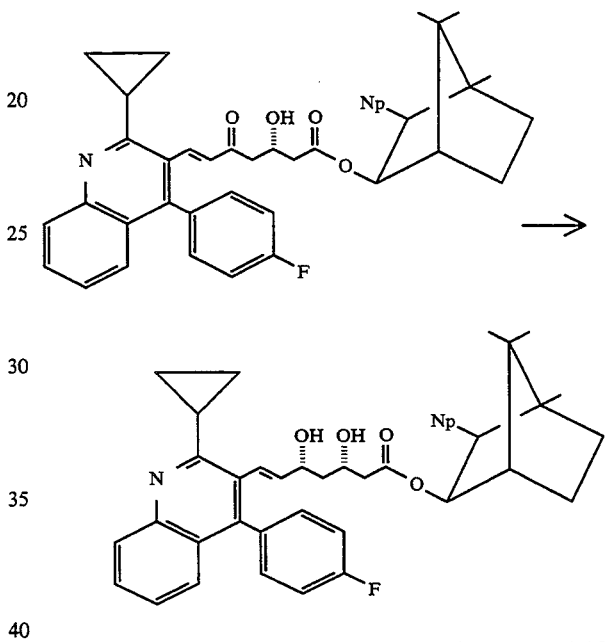

The hydroxycarboxylic acid ester (102 mg, 0.15 mmol) obtained in Example 19 was dissolved in a solvent mixture of THF (2.0 ml) and methanol (0.5 ml). Diethylmethoxyborane (16 mg, 0.16 mmol) was added thereto at −78° C. under argon atmosphere. The mixture was stirred at −78° C. to room temperature over 15 minutes and cooled again at −78° C. Sodium borohydride (28 mg, 0.74 mmol) was added thereto. After stirring at −78° C. for 4 hours and at −78° C. to room temperature over 8 hours, the mixture was treated with acetic acid (0.5 ml) to quench the reaction, poured into saturated sodium hydrogen carbonate aq solution and finally extracted with diethyl ether. The organic layer was washed with saturated sodium chloride aq solution, dried over anhydrous magnesium sulfate and then concentrated in vacuo. Methanol (10 ml) was added to dissolve the residue and then removed in vacuo. This operation was repeated 10 times to decompose and evaporate organoboron compounds. The resulting crude product was purified by column chromatography (hexane:ethyl acetate=15:1) to give (4S)-4,7,7-trimethyl-3-exo-(1-naphthyl)bicyclo[2.2.1]heptan-2-exo-yl (3S,5R,6E)-7-{2-cyclopropyl-4-(4-fluorophenyl)quinolin-3-yl}-3,5-dihydroxy-6-heptenoate (87 mg, 85% yield) $R_f$=0.36 (hexane:AcOEt=2:1) $[\alpha]_D^{20}$ = −73.78° (c 1.03, CHCl$_3$) IR (CHCl$_3$): 3460, 3010, 2960, 1725, 1605, 1515, 1490, 1400, 1220, 1090, 790 cm$^{-1}$.

¹H NMR (CDCl₃): δ=0.80 (d, J=14.3 Hz, 1H), 0.88-0.96 (m, 1H), 1.02 (s, 3H), 1.00-1.05 (m, 2H), 1.27 (s, 3H), 1.33 (s, 3H), 1.31-1.37 (m, 2H), 1.46-1.55 (m, 1H), 1.57-1.63 (m, 2H), 1.75-1.82 (m, 1H), 1.83 (dd, J=15.4, 9.4 Hz, 1H), 1.92-1.98 (m, 1H), 2.00 (d, J=4.8 Hz, 1H), 2.39 (m, 1H), 2.92-2.99 (m, 1H), 3.03 (d, J=1.4 Hz, 1H), 3.95-3.99 (m, 1H), 4.08 (d, J=8.5 Hz, 1H), 5.40 (dd, J=16.2, 5.8 Hz, 1H), 5.52 (d, J=8.5 Hz, 1H), 6.50 (dd, J=16.2, 1.4 Hz, 1H), 7.07-7.18 (m, 4H), 7.27-7.34 (m, 2H), 7.38-7.44 (m, 2H), 7.50 (dd, J=7.0, 1.5 Hz, 1H), 7.58 (dd, J=6.3, 2.0 Hz, 1H), 7.65 (d, J=7.3 Hz, 1H), 7.69 (d, J=8.2 Hz, 1H), 7 80 (dd, J=8.0, 1.2 Hz, 1H), 7 94 (d, J=7.7 Hz, 1H), 8.04 (d, J=8.5 Hz, 1H). MS: m/z (rel intensity) 683 (M⁺, 1) 665 (M+-H₂O, 0.3) 644 (1), 420 (16), 288 (53), 275 (34), 170 (100).

REFERENTIAL EXAMPLE 13

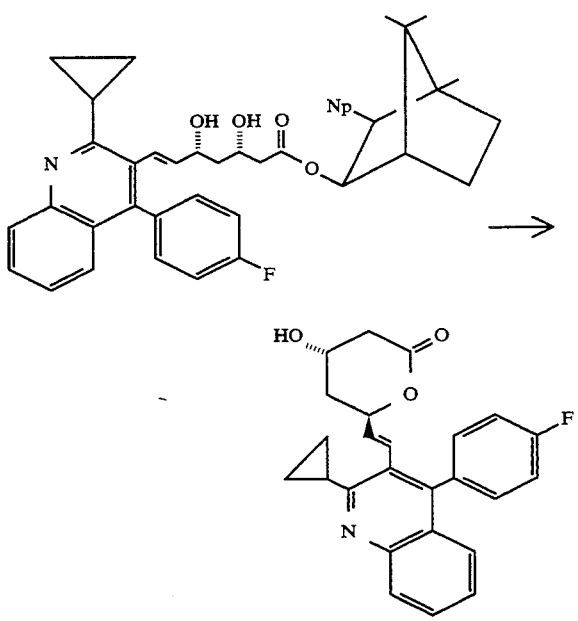

Aqueous 1M sodium hydroxide solution (0.5 ml, 0.10 mmol) was added to a methanol (5.0 ml) solution of the dihydroxyester (60 mg, 0.09 mmol) obtained in Example 20. The mixture was stirred at room temperature for 12 hours. Then, the resulting mixture was poured into sodium acetate-acetic acid buffer (15 ml, pH=4-5) and extracted with ethyl acetate. The organic layer was washed with saturated sodium chloride aq solution, dried over anhydrous magnesium sulfate, and concentrated in vacuo. The residue was subjected to preparative thin layer chromatography (hexane:ethyl acetate=1:1) to separate the desired product from (4S)-4,7,7-trimethyl-3-exo-(1-naphthyl)bicyclo[2.2.1]heptan-2-exo-ol (22 mg, 90%). The desired product was then dissolved in toluene (25 ml), and the solution was heated under reflux for 12 hours. After removing the toluene in vacuo, the residue was purified by preparative thin layer chromatography (hexane:ethyl acetate=1:2) to give (3S,5R,6E)-7-{2-cyclopropyl-4-(4-fluorophenyl)-quinolin-3-yl}-3,5-dihydroxy-6-hepten-1,5-olide (16 mg, 45% yield) as colorless foam. HPLC analysis (CHIRALPACK AS, hexane:isopropyl alcohol=9:1) of the product showed a cis:trans ratio of 96:4 and an optical purity of 93% ee. R_f=0.19 (hexane:AcOEt=2:1) [α]_D²⁰=+6.98° (c 1.74, CHCl₃) IR (CHCl₃): 3440, 3005, 1730, 1600, 1560, 1510, 1490, 1410, 1230, 1155, 1060, 970, 830, 730 cm⁻¹.

¹H NMR (CDCl₃): δ=1.03-1.08 (m, 2H), 1.30-1.40 (m, 2H), 1.56-1.60 (m, 1H), 1.78 (m, 1H), 2.38 (m, 1H), 2.60 (ddd, J=7.4, 4.0, 1.5 Hz, 1H), 2.70 (dd, J=13.0, 4.8 Hz, 1H), 4.25 (m, 1H), 5.18 (m, 1H), 5.62 (dd, J=16.1, 6.2 Hz, 1H), 6.72 (dd, J=16.1, 1.4 Hz, 1H), 7.17-7.25 (m, 4H), 7.30-7.37 (m, 2H), 7.61 (dd, J=6.1, 2.1 Hz, 1H), 7.96 (d, J=8.3 Hz, 1H). MS: m/z (rel. intensity) 403 (M⁺, 9), 316 (11), 288 (100), 274 (12).

EXAMPLE 21

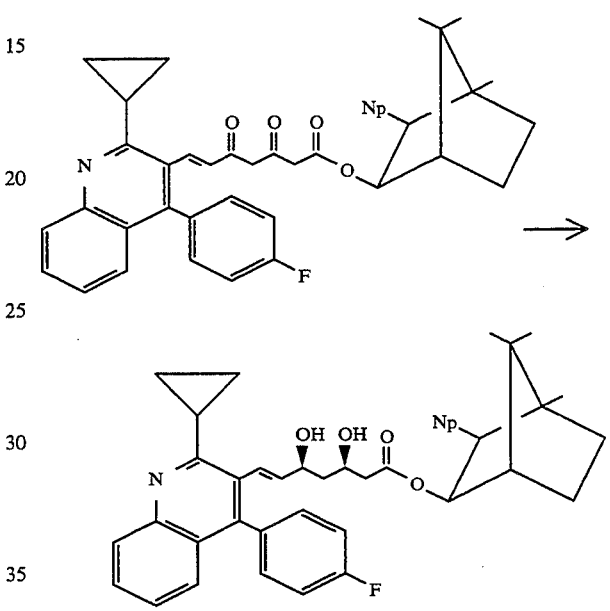

The diketocarboxylic acid ester (100 mg, 0.15 mmol) obtained in Example 17 was dissolved in a solvent mixture of THF (2.0 ml) and methanol (0.5 ml). Dimethylethoxyborane (14 mg, 0.16 mmol) was added thereto at −78° C., and the whole was stirred for 15 minutes. Thereto was added sodium borohydride (28 mg, 0.74 mmol). After stirring at −78° C. for 4 hours and at −78° C. to room temperature over 8 hours, the mixture was treated with acetic acid (0.5 ml) to terminate the reaction, poured into saturated sodium hydrogen carbonate aq solution and then extracted with diethyl ether. The organic layer was washed with saturated sodium chloride aq solution, dried over magnesium sulfate, and concentrated in vacuo. Methanol (10 ml) was added to dissolve the residue and then removed in vacuo. This operation was repeated 10 times to decompose and evaporate organoboron compounds. The resulting crude product was purified by column chromatography (hexane:ethyl acetate=3:1) to give (4S)-4,7,7-trimethyl-3-exo-(1-naphthyl)-bicyclo[2.2.1]heptan-2-exo-yl (3R,5S,6E)-7-{2-cyclopropyl-4-(4-fluorophenyl)-quinolin-3-yl}-3,5-dihydroxy-6-heptenoate (95 mg, 94% yield). R_f=0.36 (hexane:AcOEt=2:1) [α]_D²⁰=−75.29° (C 1.02, CHCl₃) IR (CHCl₃): 3460, 3010, 2960, 1725, 1605, 1515, 1490, 1400, 1220, 1090, 790 cm⁻¹.

¹H NMR (CDCl₃): δ=0.75-0.96 (m, 2H), 1.02 (s, 3H), 1.00-1.05 (m, 2H), 1.27 and 1.26 (s, 3H), 1.33 and 1.32 (s, 3H), 1.31-1.37 (m, 2H), 1.46-1.55 (m, 1H), 1.57-1.63 (m, 2H), 1.75-1.98 (m, 3H), 2.00 (br s, 1H), 2.39 (m, 1H), 2.92-2.99 (m, 1H), 3.09 and 3.17 (m, 1H), 3.95-3.99 (m, 1H), 4.08 (br d, J=8.5 Hz, 1H), 5.36-5.47

(m, 1H), 5.51–5.58 (m, 1H), 6.50 and 6.51 (dd, J=16.2, 1.4 Hz, 1H), 7.07–7.18 (m, 4H), 7.27–7.34 (m, 2H), 7.38–7.52 (m, 3H), 7.55–7.83 (m, 4H), 7.94 (m, 1H), 8.04 (m, 1H). MS: m/z (rel. intensity) 683 (M+, 12), 642 (0.3), 420 (41), (13), 288 (78), 275 (34), 263 (100), 207 (74), 170 (93).

REFERENTIAL EXAMPLE 14

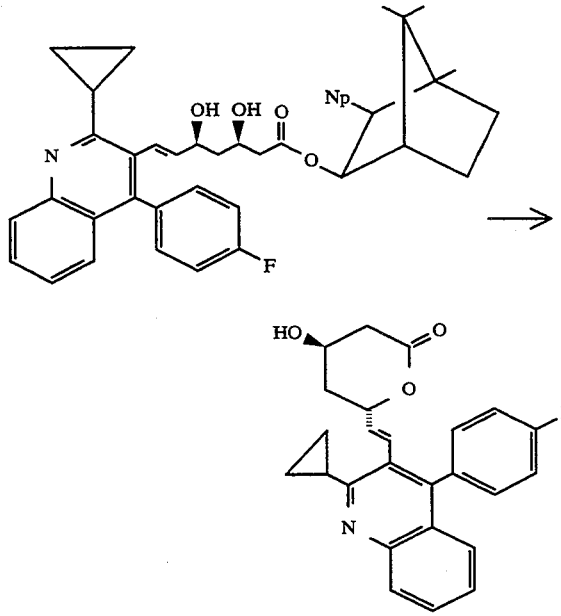

Aqueous 1M sodium hydroxide solution (0.5 ml) was added to a methanol (5.0 ml) solution of the dihydroxyester (90 mg, 0.13 mmol) obtained in Example 21. The mixture was stirred at room temperature for 12 hours. Then, the resulting mixture was poured into sodium acetate-acetic acid buffer (15 ml, pH=4–5) and extracted with ethyl acetate. The organic layer was washed with saturated sodium chloride aq solution, dried over anhydrous magnesium sulfate, and concentrated in vacuo. The residue was subjected to preparative thin layer chromatography (hexane:ethyl acetate=1:1) to separate the desired product from (4S)-4,7,7-trimethyl-3-exo-(1-naphthyl)bicyclo[2.2.1]heptan-2-exo-ol (33 mg, 90%). The desired product was then dissolved in toluene (25 ml), and the solution was heated under reflux for 12 hours. After removing the toluene in vacuo, the residue was purified by preparative thin layer chromatography (hexane:ethyl acetate=1:2) to give of (3R,5S,6E)-7-{2-cyclopropyl-4-(4-fluorophenyl)quinolin-3-yl}-3,5-dihydroxy-6-hepten-1,5-olide (26 mg, 48% yield) as colorless foam. HPLC analysis (CHIRALPACK AS, hexane:isopropyl alcohol=9:1) of the product showed a cis:trans ratio of 64:36 and an optical purity of 37% ee. $R_f$=0.19 (hexane:AcOEt=2:1) $[\alpha]_D^{20}$= −20.90° (c 0.56 CHCl$_3$) IR (CHCl$_3$): 3440, 3005, 1730, 1600, 1560, 1510, 1490, 1410, 1230, 1155, 1060, 970, 830, 730 cm$^{-1}$.

$^1$H NMR (CDCl$_3$): δ=1.03–1.08 (m, 2H), 1.30–1.40 (m, 2H), 1.56–1.60 (m, 1H), 1.78 (m, 1H), 2.38 (m , 1H), 2.60 (ddd, J=7.4, 4.0, 1.5 Hz, 1H), 2.70 (dd, J=13.0, 4.8 Hz, 1H), 4.25 (m, 1H), 5.18 and 4.66 (m, 1H, ratio 64:36), 5.62 (dd, J=16.1, 6.2 Hz, 1H), 6.72 (dd, J=16.1, 1.4 Hz, 1H), 7.17–7.25 (m, 4H), 7.30–7.37 (m, 2H), 7.61 (dd, J=6.1, 2.1 Hz, 1H), 7.96 (d, J=8.3 Hz, 1H). MS: m/z (rel intensity) 403 (M+, 9) 316 (11), 288 (100) 274 (12)

What is claimed is:

1. An optically active ester of β,δ-syn-dihydroxycarboxylic acid represented by the following formula (IV):

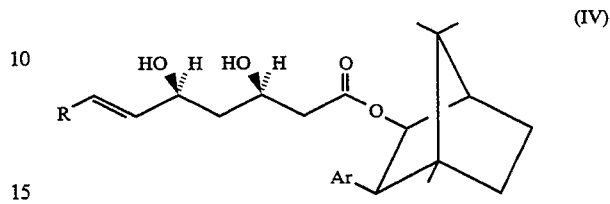

wherein

R is a phenyl group optionally substituted with one to four substituents selected from the group consisting of a C$_1$-C$_3$ alkyl group, a halogen, a C$_1$-C$_3$ alkoxy group, and a phenyl group optionally substituted with a halogen, a C$_1$-C$_3$ alkyl group or both a halogen and C$_1$-C$_3$ alkyl group;

a vinyl group substituted with two or three substituents selected from the group consisting of a C$_1$-C$_3$ alkyl group, a phenyl group optionally substituted with a halogen, a C$_1$-C$_3$ alkyl group or both a halogen and C$_1$-C$_3$ alkyl group, and a 1H-tetrazolyl group optionally substituted with a halogen, a C$_1$-C$_3$ alkyl group or both a halogen and C$_1$-C$_3$ alkyl group;

a pyridyl group optionally substituted with one to four substituents selected from the group consisting of a halogen, a cyclopropyl group, an oxo group, a C$_1$-C$_3$ alkyl group optionally substituted with benzyloxy group, and a phenyl group optionally substituted with a halogen, a C$_1$-C$_3$ alkyl group or both a halogen and C$_1$-C$_3$ alkyl group; or a pyridyl group condensed with benzene ring, pyrazole ring, or thiophene ring, optionally substituted with one to four substituents selected from the group consisting of a halogen, a cyclopropyl group, an oxo group, a C$_1$-C$_4$ alkyl group optionally substituted with benzyloxy group, and a phenyl group optionally substituted with a halogen, a C$_1$-C$_3$ alkyl group or both a halogen and C$_1$-C$_3$ alkyl group; and Ar is a condensed aromatic group, or an enantiomer thereof.

2. An optically active enantio-ester of β,δ-syn-dihydroxycarboxylic acid represented by the following formula (V):

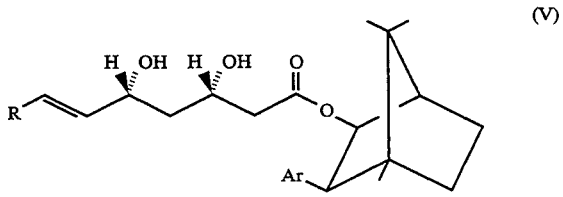

wherein

R is a phenyl group optionally substituted with one to four substituents selected from the group consisting of a C$_1$-C$_3$ alkyl group, a halogen, a C$_1$-C$_3$ alkoxy group, and a phenyl group optionally substituted with a halogen, a $C_1$–$C_3$ alkyl group or both a halogen and $C_1$–$C_3$ alkyl group;

a vinyl group substituted with two or three substituents selected from the group consisting of a $C_1$–$C_3$ alkyl group, a phenyl group optionally substituted with a halogen, a $C_1$–$C_3$ alkyl group or both a halogen and $C_1$–$C_3$ alkyl group, and a 1H-tetrazolyl group optionally substituted with a halogen, a $C_1$–$C_3$ alkyl group or both a halogen and $C_1$–$C_3$ alkyl group;

a pyridyl group optionally substituted with one to four substituents selected from the group consisting of a halogen, a cyclopropyl group, an oxo group, a $C_1$–$C_3$ alkyl group optionally substituted with benzyloxy group, and a phenyl group optionally substituted with a halogen, a $C_1$–$C_3$ alkyl group or both a halogen and a $C_1$–$C_3$ alkyl group; or a pyridyl group condensed with benzene ring, pyrazole ring, or thiophene ring, optionally substituted with one to four substituents selected from the group consisting of a halogen, a cyclopropyl group, an oxo group, a $C_1$–$C_4$ alkyl group optionally substituted with benzyloxy group, and a phenyl group optionally substituted with a halogen, a $C_1$–$C_3$ alkyl group or both a halogen and $C_1$–$C_3$ alkyl group; and Ar is a condensed aromatic group, or an enantiomer thereof.

3. The ester according to claim 1 or 2 wherein Ar is selected from the group consisting of naphthyl group, anthryl group, and phenanthryl group.

4. The ester according to claim 1 or 2 wherein the pyridyl group condensed with benzene ring, pyrazole ring or thiophene ring, is selected from the group consisting of quinolin-3-yl group, pyrazolo[3,4-b]pyridin-5-yl, and thieno[2,3-b]pyridin-5-yl-group.

5. An ester according to claim 1 or 2, wherein R is a phenyl group; a substituted phenyl selected from the group consisting of 4-tolyl, 4-chlorophenyl, 4-methoxyphenyl, 3,5-dichloro-6-(4-fluorophenyl)phenyl, and 2,4-dimethyl-6-(4-fluoro-3-methylphenyl)phenyl; a substituted pyridyl selected from the group consisting of 4-phenyl-2-methylpyridin-3-yl, 2-isopropyl-6-phenyl-4-(4-fluoro-phenyl)pyridin-3-yl, 2,5-diisopropyl-4-(4-fluorophenyl)-pyridin-3-yl, 2,6-diisopropyl-4-(4-fluorophenyl)-5-benzyloxymethylpyridin-3-yl, 6-cyclopropyl-4-(4-fluoro-phenyl)-1,3-dimethylpyrazolo[3,4-b]pyridin-5-yl, 4-(4-fluorophenyl)-1,3-dimethyl-6-(1-methylethyl)pyrazolo[3,4-b]pyridin-5-yl, 1-t-butyl-6-cyclopropyl-4-(4-fluorophenyl)-3-methylpyrazolo[3,4-b]pyridin-5-yl, 1-t-butyl-6-cyclopropyl-4-(4-fluorophenyl)-3-phenylpyrazolo[3,4-b]pyridin-5-yl, 6-cyclopropyl-4-(4-fluorophenyl)thieno[2,3-b]pyridin-5-yl, and 6-cyclopropyl-3-ethyl-4-(4-fluorophenyl)-2-methylthieno[2,3-b]pyridin-5-yl; a substituted quinolyl selected from the group consisting of 3-isopropyl-1-(4-fluorophenyl)-4-oxoquinolin-2-yl, 2-cyclopropyl-4-(4-fluorophenyl)-quinolin-3-yl, 4-(4-fluorophenyl)-2-(1-methylethyl)-quinolin-3-yl, 6-chloro-2-(1-methylethyl)-4-phenyl-quinolin-3-yl, 4-(4-fluorophenyl)-6-methyl-2-(1-methylethyl)quinolin-3-yl, and 2-cyclopropyl-4-(4-fluorophenyl)-8-methylquinolin-3-yl; or a substituted vinyl selected from the group consisting of 2,2-diphenylethenyl, 1-isopropyl-2,2-bis(4-fluorophenyl)ethenyl, and 1-(1-methyl-1H-tetrazol-5-yl)-2,2-(4-fluorophenyl)ethenyl.

* * * * *